US009623096B2

(12) United States Patent
Conrad et al.

(10) Patent No.: US 9,623,096 B2
(45) Date of Patent: Apr. 18, 2017

(54) VIRALLY INFECTED HEMATOPOIETIC CELLS AND USES THEREOF

(71) Applicant: Celverum Inc., Ottawa (CA)

(72) Inventors: David Conrad, Ottawa (CA); John Cameron Bell, Ottawa (CA); Harry Atkins, Ottawa (CA)

(73) Assignee: Celverum Inc., Ottawa (CA)

( * ) Notice: Subject to any disclaimer, the term of this patent is extended or adjusted under 35 U.S.C. 154(b) by 101 days.

(21) Appl. No.: 13/672,190

(22) Filed: Nov. 8, 2012

(65) Prior Publication Data

US 2013/0115243 A1    May 9, 2013

Related U.S. Application Data

(60) Provisional application No. 61/557,634, filed on Nov. 9, 2011.

(51) Int. Cl.
*A61K 39/00* (2006.01)
*C12N 5/09* (2010.01)

(52) U.S. Cl.
CPC ........ *A61K 39/0011* (2013.01); *C12N 5/0693* (2013.01); *C12N 5/0694* (2013.01); *A61K 2039/5152* (2013.01); *A61K 2039/5156* (2013.01); *C12N 2510/00* (2013.01); *C12N 2760/20032* (2013.01); *C12N 2770/36032* (2013.01)

(58) Field of Classification Search
CPC .... C07K 14/475; C07K 14/52; C07K 14/005; C07K 14/4748; C07K 14/521; C07K 16/00; C07K 16/2875; C07K 16/2896; C07K 14/535; C07K 14/55; C07K 14/57; A61K 39/0011; A61K 38/00; A61K 38/19; A61K 35/28; A61K 35/761; A61K 35/768; A61K 2039/5158; A61K 2039/515; A61K 35/76; A61K 2039/6006; A61K 39/00; A61K 39/39558; C12N 5/00; C12N 5/006; C12N 5/06; C12N 5/0602; C12N 5/0693; C12N 2500/70; C12N 2700/00; C12N 2720/12232; C12N 2720/12243; C12N 5/0093; C12N 5/0634; C12N 2720/00; Y10S 514/885
See application file for complete search history.

(56) References Cited

U.S. PATENT DOCUMENTS 4,108,983 A    8/1978  Wallack
2001/0048919 A1 * 12/2001 Morris et al. ............... 424/93.21
2012/0058141 A1 *  3/2012 Palese et al. ............... 424/199.1

OTHER PUBLICATIONS

Schuepbach et al., Blood, 1983, 62:616-621.*
Hsu et al., Clin. Exp. Immunol., 2001, 126:84-91.*
Tumilasci et al., Journal of Virology, Published Ahead of Print Jun. 2008, 82(17):8487-8499.*
Stojdl et al., Cancer Cell, 2003, 4:263-275.*
Brun et al., The American Society of Gene & Cell Therapy, published online Jun. 2010, 18(8):1440-1449.*
Miller et al., Protein Expression and Purification, 2004, 33:92-103.*
Huang et al., Cancer Letters, 2003, 202:153-159.*
Haas et al., Cancer Immunol Immunother, 1996, 43:190-194.*
Ravindra et al., Indian J Med Res 130, Nov. 2009, pp. 507-513.*
Paglino et al., Journal of Virology, Sep. 2011, 85(18):9346-9358.*
Connor et al., Journal of Virology, Sep. 2004, 78(17):8960-8970.*
Bridle, Byram, W. et al., "Vesicular Stomatitis Virus as a Novel Cancer Vaccine Vector to Prime Antitumor Immunity Amenable to Rapid Boosting With Adenovirus" Molecular Therapy: The American Society of Gene and Cell Therapy, Oct. 2009, p. 1814-1821, vol. 17 No. 10.
Castle, John, C. et al., "Exploiting the Mutanome for Tumor Vaccination" Cancer Research, Jan. 11, 2012, p. 1081-1091.vol. 72.
Contag, Christopher, H. et al.,"Definition of an Enhance Immune Cell Therapy in Mice That Can Target Stem-Like Lymphoma Cells" Cancer Research, Oct. 8, 2010, p. 9837-9845, vol. 70.
Eager, et al., "Clinical development directions in oncolytic viral therapy" Cancer Gene Therapy, Mar. 25, 2011, p. 305-317, vol. 18.
Fielding, "Current Therapeutic Strategies in Adult Acute Lymphoblastic Leukemia", Hematology/Oncology Clinics of North America, Dec. 2011, p. 1255-1279, vol. 25, Elsevier Inc.
Irvine, Kari, R. et al., "Enhancing Efficacy of Recombinant Anticancer Vaccines With Prime/Boost Regimens That Use Two Different Vectors" Journal of National Cancer Institute, Nov. 5, 2011, p. 1595-1601, vol. 89, No. 21.
Jansson, Johan et al., "Acute lymphoblastic Leukemia cells that survive combination chemotherapy in vivo remain sensitive to allogeneic immune effects", Leukemia Research, Jun. 2011, p. 800-807, vol. 35.
Krueger, Karl, E. et al.,"Posttranslational Protein Modifications: Current Implications for Cancer Detection, Prevention, and Therapeutics" Molecular & Cellular Proteomics 5.10, Jul. 14, 2006, p. 1799-1810.
Lichty, Brian, D. et al., "Vesicular Stomatitis Virus: A Potential Therapeutic Virus for the Treatment of Hematologic Malignancy", Human Gene Therapy, Sep. 2004, p. 821-831, vol. 15.
Mellman, Ira et al. "Cancer immunotherapy comes of age" Nature, Dec. 2011, p. 480-489, vol. 480.
Petersen, Jan et al. "Post-translationally modified T cell epitopes: immune recognition and immunotherapy" Journal of Molecular Medicine, Sep. 2009, p. 1045-1051, vol. 87.

(Continued)

*Primary Examiner* — Nicole Kinsey White
(74) *Attorney, Agent, or Firm* — Suzannah K. Sundby, Esq.; Canady + Lortz LLP

(57) ABSTRACT

An immunogenic formulation for a patient, the formulation includes virus-modulated hematopoietic cancer cells, where the modulated hematopoietic cancer cells are generated from viable hematopoietic cancer cells obtained from the patient, either isolated or in a mixed hematopoietic population of healthy and cancer cells, and where the viable hematopoietic cancer cells are infected ex vivo with a virus that modulates the expression of a plurality of endogenous immune regulatory molecules to increase the immunogenicity of the hematopoietic cancer cells.

17 Claims, 25 Drawing Sheets

(56) References Cited

OTHER PUBLICATIONS

Pulido, Jose et al. "Using virally expressed melanoma cDNA libraries to identify tumor-associated antigens that cure melanoma" Nature Biotechnology, Apr. 2012, p. 337-344, vol. 30, No. 4.
Ram, Ron et al."Non-myeloablative conditioning with allogeneic hematopoietic cell transplantation for the treatment of high-risk acute lymphoblastic leukemia", Haematologica, Accepted Apr. 11, 2011, p. 1113-1120, vol. 96(8).
Rezvani, Katayoun et al. "Vaccination Strategies in Lymphomas and Leukaemias", Drugs, Sep. 2011, p. 1659-1674, vol. 71(13).
Rousseau, Raphael et al. "Immunotherapy of high-risk acute leukemia with a recipient (autologous) vaccine expressing transgenic human CD4OL and 1L-2 after chemotherapy and allogeneic stem cell transplantation", Blood, Feb. 15, 2006, p. 1332-1341, vol. 107, No. 4.
Stripecke, R. et al., "Immunotherapy with acute leukemia cells modified into antigen-presenting cells: ex vivo culture and gene transfer methods", Leukemia, Oct. 2002, p. 1974-1983, vol. 16.
Brun, Jan et al. "Identification of Genetically Modified Maraba Virus as an Oncolytic Rhabdovirus", Molecular Therapy: The American Society of Gene and Cell Therapy, Aug. 2010, p. 1440-1449, vol. 18 No. 8.
Brown, Christopher, W. et al. "The p14 FAST Protein of Reptilian Reovirus Increases Vesicular Stomatitis Virus Neuropathogenesis" Journal of Virology, Jan. 2009, p. 552-561, American Society for Microbiology.
Breitbach, Caroline, J. et al. "Targeted Inflammation During Oncolytic Virus Therapy Severely Compromises Tumor Blood Flow" Molecular Therapy: The American Society of Gene Therapy, Sep. 2007, p. 1686-1693, vol. 15 No. 9.

\* cited by examiner

A.301

L1210

OCI-Ly18

EL4

Jurkat

US 9,623,096 B2

VIRALLY INFECTED HEMATOPOIETIC CELLS AND USES THEREOF

FIELD

The present disclosure relates generally to cancer treatment, particularly immunogenic formulations for raising an anti-cancer immune response in a patient.

BACKGROUND

The treatment of acute hematologic malignancies may involve various modalities including intensified chemotherapy, radiation, and blood or bone marrow transplantation. Unfortunately, most patients still succumb to the underlying malignancy or the associated treatment regimens. For example, in patients younger than 60 years of age with acute myelogenous leukemia (AML) and enrolled in clinical studies, overall survival remains less than 40%. In adults with acute lymphoblastic leukemia (ALL) and favorable genetics, similar overall rates of survival are observed.

After achieving leukemic remission, a minority of patients are eligible to receive consolidative high dose therapy (HDT) followed by allogeneic hematopoietic stem and progenitor cell transplantation. In some patients this maneuver results in a cure due to the donor-derived immunological effect of graft versus leukemia. However, these patients unfortunately may also acquire chronic multi-organ damage from graft versus host disease—where the same donor-derived immunological phenomenon is directed at normal tissue. Graft versus host disease has an associated mortality rate of 10-30%. Even so, the majority of adult patients with these acute leukemias are too old to be considered candidates for HDT. The overall survival rate for these patients is less than 10%.

Oncolytic virus-derived therapies are therapies that use viruses either to directly lyse the tumour cells or, if modified, as vectors to infect the tumor cells with genes that encode specific tumor-associated antigens.

Oncolytic viruses (OVs) have been engineered to be dependent upon tumor-specific constitutively activated regulatory pathways. The selective anti-tumor activities of an OV include: direct cytolysis, apoptosis, virus-mediated synctium formation with intra-tumoral viral spread, activation of peri-tumor inflammation and intratumoral coagulation with ischemic necrosis.

Oncolytic virus-derived therapies take advantage of deficiencies of innate immunity which develop in many hematopoietic cancer cells as they acquire their proliferative phenotype. For example, this can involve perturbations in the RAS, DAF, STAT and/or interferon regulatory pathways. OVs have evolved to exploit these immune defects for replication advantage. Infection of a permissive hematopoietic cancer cell with an oncolytic virus results in cell lysis and viral spread to adjacent tumor tissue. Healthy cells with intact innate defenses resist and eliminate the viral threat. Such oncolytic virus-derived therapies may have an impressive therapeutic index, particularly when using a modified virus with deletions in wild-type genes normally responsible for mitigating a cell's anti-viral defense.

Examples of oncolytic virus-derived therapies include vaccines made from virally modified tumor cell lysates. Such vaccines are also known as viral oncolysates and in such vaccines the OV is used to infect and rupture a tumor cell, thereby producing a mixture of cellular debris, which is used to potentially stimulate the immune response in a patient. The cellular debris may be considered to be the antigenic material, while the viruses may be considered to be an adjuvant. Such vaccines are often lysed using mechanical methods in order to produce the mixture of cellular debris.

One problem with cancer vaccines which have been engineered to contain specific tumor antigen peptide(s) is that antigen presentation by antigen presenting cells (APCs) remains inefficient using standard vaccine approaches. APC processing of a single or few tumor peptide(s) likely does not lead to an anti-tumor T-cell response with adequate breadth to significantly impact survival.

Other examples of oncolytic virus-derived therapies include pharmaceutical compositions comprising human leukocytes and replication-competent OVs (see U.S. Pat. No. 7,595,042). The compositions taught in U.S. Pat. No. 7,595,042 use isolated leukocyte cells to protect the virus from neutralizing antibody in a patient, thereby delivering the OV to tumors. This is an advantage over freely injected OVs, which expose the virus to the neutralizing antibody in patients that have generated an immune response, thereby rendering the virus non-infectious.

A review of immunotherapy using acute leukemia cells modified using gene transfer methods to generate functional antigen presenting cells was published in *Leukemia* (2002) 16, 1974-1983.

Although modest efficacy has been reported using viruses as "oncolysates" in the treatment of solid cancers, non-solid cancers or acute hematologic malignancies such as AML or ALL are difficult to treat with OVs in-situ.

SUMMARY

In one aspect, the present disclosure provides an immunogenic formulation for a patient, the formulation includes infected hematopoietic cancer cells, where the infected hematopoietic cancer cells are generated from viable hematopoietic cancer cells obtained from the patient and where the viable hematopoietic cancer cells are infected ex vivo with a virus that modulates the expression of a plurality of endogenous immune regulatory molecules to increase the immunogenicity of the infected hematopoietic cancer cells.

The cancer cells may be purified or isolated and then infected. Alternatively, the cancer cells may be infected while in whole blood or whole bone marrow samples obtained from the patient. The formulation may impart an anti-tumor immune response in a patient receiving the formulation.

The virus may be a virus of the Rhabdoviridae family, the Togaviridae family, the Leporipoxvirus family, the Reoviridae family, the Paramyxovirus family, or the Picornavirus family.

The virus may be a virus of the Togaviridae family, where the virus is a semliki forest virus. The virus may be a virus of the Rhabdoviridae family, where the virus is a vesicular stomatitis Indiana virus, a maraba virus, a carajas virus, or a chandipura virus.

The virus may be a rhabdovirus with interferon dependent and independent attenuating deletions in the matrix and glycoprotein proteins, respectively.

The virus may be a Vesicular Stomatitis Virus which is modified to be sensitive to the antiviral effects of type I interferons. The Vesicular Stomatitis Virus may be modified by deletion of the $51^{st}$ amino acid in the M protein.

The Vesicular Stomatitis Virus may be modified to reduce the ability of the virus to spread to other cells. The Vesicular Stomatitis Virus may be modified by deletion of the gene encoding G-protein.

The immunogenic formulation may include at least 100 infected hematopoietic cancer cells.

The immune regulatory molecules may be: immunomodulatory molecules released by the cell, immunomodulatory markers expressed on the cell surface, or any combination thereof. The immune regulatory molecules may be inside the cell, before they are released by the cell, or expressed on the cell surface.

The immunomodulatory molecules released by the cell may be cytokines or proteins or any combination thereof. The cytokines may be: CCL4, IL-6, interferon-γ, IL-2, IL-12, IL-15, or any combination thereof. The proteins may be calreticulin. The immunomodulatory markers expressed on the cell surface may be: CD40, OX40 ligand, Inducible costimulator-ligand ("ICOS-L"), OX40 ("CD134"), ICOS ("CD278"), CD137, CD137 ligand, CD40 ligand, CD28, CD95, FAS, FAS ligand, Chemokine (C-C motif) ligand 5 ("CCL5" or "RANTES"), calreticulin or any combination thereof.

The infected hematopoietic cancer cells may be intact, or may be partially destroyed after infection with the virus. Partial destruction of the cells may be by, for example, freeze thawing or treatment with paraformaldehyde.

In another aspect, the present disclosure provides an immunogenic formulation for a patient, the formulation includes hematopoietic cancer cells in association with a virus that modulates the expression of a plurality of endogenous immune regulatory molecules to increase the immunogenicity of the infected hematopoietic cancer cells, where the hematopoietic cancer cells are generated from viable hematopoietic cancer cells obtained from the patient and where the viable hematopoietic cancer cells are infected ex vivo with the virus and then destroyed by further treatment while retaining the virally-induced immune regulatory molecules. The further treatment may be, for example, freeze thawing or treatment with paraformaldehyde.

In another aspect, the present disclosure provides a method of preparing the immunogenic formulation. The method includes: obtaining viable hematopoietic cancer cells from the patient; infecting, ex vivo, the obtained viable hematopoietic cancer cells with the virus that modulates the expression of a plurality of endogenous immune regulatory molecules to increase the immunogenicity of the infected hematopoietic cancer cells; and incubating the infected hematopoietic cancer cells to generate the infected hematopoietic cancer cells.

The obtained viable hematopoietic cancer cells may be infected with viral particles in a ratio of at least 1 viral particle to 100 hematopoietic cancer cells. In particular examples, the obtained viable hematopoietic cancer cells may be infected with viral particles in a ratio of at least 1 viral particle to 1 hematopoietic cancer cell, or for example at least 10 viral particles to 1 hematopoietic cancer cell.

The infected hematopoietic cells may be incubated for at least a single gene replication cycle of the virus. If the virus is a rhabdovirus, the single gene replication cycle may be around 30 minutes.

In another aspect, the present disclosure provides a method of prolonging the length of time until a hematopoietic cancer relapses in a patient post-treatment. The method includes: administering to the patient an effective amount of an immunogenic formulation according to the application.

In yet another aspect, the present disclosure provides a method of treating a hematopoietic cancer in a patient. The method includes: administering to the patient an effective amount of an immunogenic formulation according to the application.

In still another aspect, the present disclosure provides a method of inducing an anti-cancer immune response in a patient. The method includes: administering to the patient an effective amount of an immunogenic formulation according to the application.

In another aspect, the present disclosure provides an immunogenic formulation to induce an anti-cancer immune response in a patient, where the immunogenic formulation comprises infected hematopoietic cancer cells, and where: the infected hematopoietic cancer cells are generated from viable hematopoietic cancer cells obtained from the patient and where the viable hematopoietic cancer cells are infected ex vivo with a virus that modulates the expression of a plurality of endogenous immune regulatory molecules to increase the immunogenicity of the infected hematopoietic cancer cells.

In yet another aspect, the present disclosure provides a use of a virus in the preparation of an immunogenic formulation for inducing an anti-cancer immune response in a patient, where the immunogenic formulation comprises infected hematopoietic cancer cells obtained from the patient, where the virus modulates the expression of a plurality of endogenous immune regulatory molecules in to increase the immunogenicity of the infected hematopoietic cancer cell.

In another aspect, the present disclosure provides a kit. The kit includes a virus that modulates the expression of a plurality of endogenous immune regulatory molecules to increase the immunogenicity of infected hematopoietic cancer cells; and a container containing the virus.

The virus may be modified to include a reporter gene that encodes for a reporter protein. This reporter protein may be green fluorescent protein. The kit may further include another container, where the other container contains a virus that includes a gene that encodes for green fluorescent protein and where the virus that modulates the expression of a plurality of endogenous immune regulatory molecules lacks a gene that encodes for green fluorescent protein.

Other aspects and features of the present disclosure will become apparent to those ordinarily skilled in the art upon review of the following description of specific embodiments in conjunction with the accompanying figures.

BRIEF DESCRIPTION OF THE DRAWINGS

Examples of the present disclosure will now be described with reference to the attached Figures.

DETAILED DESCRIPTION

Figure 1A:
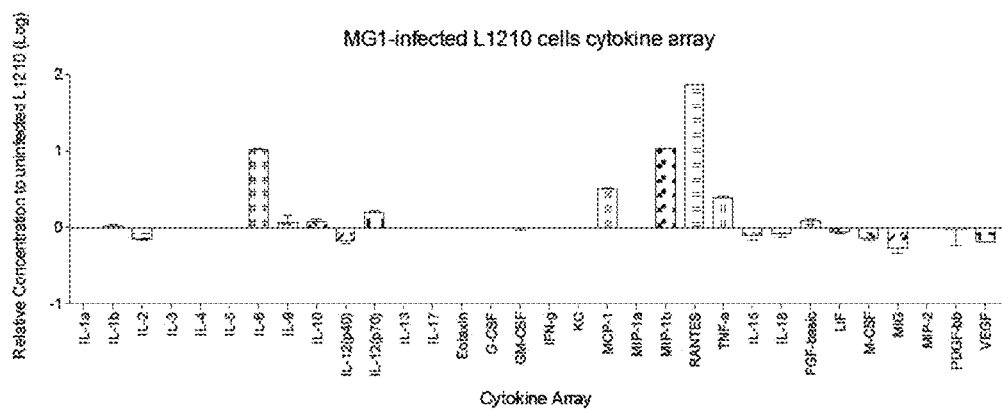
FIG. 1a is a graph illustrating a cytokine array or profile of L1210 cells infected with MG1 virus.
Figure 1B:
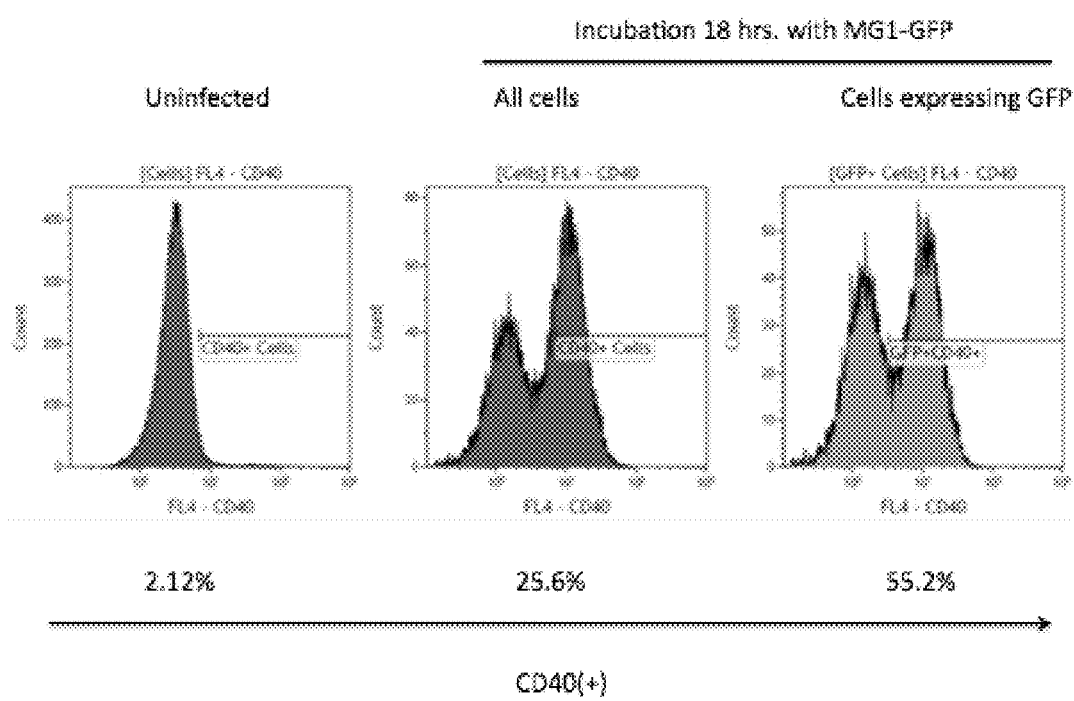
FIG. 1b are graphs of flow cytometry data illustrating the increase in CD40+ expression after viral infection of L1210 cell with MG1.

Generally, the present disclosure provides an immunogenic formulation that includes infected hematopoietic cancer cells, where the infected hematopoietic cancer cells are generated from viable hematopoietic cancer cells obtained from the patient and where the viable hematopoietic cancer cells are infected ex vivo with a virus that modulates the expression of a plurality of endogenous immune regulatory molecules to increase the immunogenicity of the infected hematopoietic cancer cells.

In another aspect, the present disclosure provides a method of preparing an immunogenic formulation, where the method includes obtaining viable hematopoietic cancer cells from the patient; infecting, ex vivo, the obtained viable hematopoietic cancer cells with the virus that modulates the expression of a plurality of endogenous immune regulatory molecules to increase the immunogenicity of the infected hematopoietic cancer cells; and incubating the infected hematopoietic cancer cells to generate the infected hematopoietic cancer cells.

The infected hematopoietic cancer cells that are generated may have enhanced immune potentiating/regulating capacity. An example of such cells are B-cell leukemia cells with rhabdovirus-induced increased expression of CD40, Ox40L and RANTES.

In still another aspect, the present disclosure provides a method of treating a hematopoietic cancer in a patient, where the method includes administering to the patient an effective amount of an immunogenic formulation that includes infected hematopoietic cancer cells, where the infected hematopoietic cancer cells are generated from viable hematopoietic cancer cells obtained from the patient and where the viable hematopoietic cancer cells are infected ex vivo with a virus that modulates the expression of a plurality of endogenous immune regulatory molecules to increase the immunogenicity of the infected hematopoietic cancer cells.

In still another aspect, the present disclosure provides a method of prolonging the length of time until a hematopoietic cancer relapses in a patient post-treatment, where the method includes administering to the patient an effective amount of an immunogenic formulation that includes infected hematopoietic cancer cells, where the infected hematopoietic cancer cells are generated from viable hematopoietic cancer cells obtained from the patient and where the viable hematopoietic cancer cells are infected ex vivo with a virus that modulates the expression of a plurality of endogenous immune regulatory molecules to increase the immunogenicity of the infected hematopoietic cancer cells.

In a further aspect, the present disclosure provides a use of an immunogenic formulation to induce an anti-cancer immune response in a patient, where the immunogenic formulation comprises infected hematopoietic cancer cells, where the infected hematopoietic cancer cells are generated from viable hematopoietic cancer cells obtained from the patient and where the viable hematopoietic cancer cells are infected ex vivo with a virus that modulates the expression of a plurality of endogenous immune regulatory molecules to increase the immunogenicity of the infected hematopoietic cancer cells. The immunogenic formulation may impart an efficient and durable anti-tumor immune response.

In still another aspect, the present disclosure provides a use of a virus in the preparation of an immunogenic formulation for inducing an anti-cancer immune response in a patient, where the immunogenic formulation comprises infected hematopoietic cancer cells obtained from the patient, where the virus modulates the expression of a plurality of endogenous immune regulatory molecules in to increase the immunogenicity of the infected hematopoietic cancer cell.

As used herein, an "endogenous immune regulatory molecule" for a cell means a gene product produced by a gene endogenous to the cell. For example, a protein produced from a gene that was already present in a cell would be considered to be an "endogenous immune regulatory molecule". On the other hand, a protein produced from a gene that was transfected into a cell would not be considered to be an "endogenous immune regulatory molecule", even if both proteins were otherwise identical.

Immunogenic Formulation.

An immunogenic formulation, also referred to as "IF", is a formulation that induces an immune response in a human or non-human animal that is treated with the formulation. The human or non-human animal is also referred to as "the patient". An immunogenic formulation made using a specific virus may be identified using the term "virus name-IF", for example "MG1-IF" or "VSVd51-IF".

The immunogenic formulation may be a formulation that induces an immune response sufficient to: reduce the growth rate of a cancer, prolong the length of time until a cancer relapses post-treatment, or both. In some examples, the immunogenic formulation induces an immune response sufficient to prevent a cancer from growing, prevent a cancer patient from relapsing post-treatment, treat an existing cancer, or any combination thereof. The immunogenic formulation may induce an immune response sufficient to prevent a cancer from relapsing after treatment with chemotherapy, radiation, surgery, blood or bone marrow transplantation, or any combination thereof.

Immunogenic formulations according to the present disclosure are generated using hematopoietic cancer cells from the patient to be treated with the formulation. The patient's hematopoietic cancer cells are infected, ex vivo, with a virus that modulates the expression of a plurality of endogenous immune regulatory molecules to increase the immunogenicity of the infected hematopoietic cancer cells. The patient's hematopoietic cancer cells may be purified or isolated and then infected, ex vivo, with the virus. Alternatively whole blood or whole bone marrow samples from patients may be infected ex-vivo without purifying or isolating the cancer cells when the virus has the ability to substantively infect cancer cells but not normal healthy cells.

Without being bound by theory, it is believed that the hematopoietic cancer cells in the immunogenic formulation may act analogous to an antigen presenting cell (APC) by the virus-induced modulation of endogenous immune regulatory molecules. Tumor antigens from the cancer cells may then be directly presented to T-cells by the hematopoietic cancer cells themselves, which are also simultaneously capable of properly stimulating the T-cells into bona fide activation and anti-cancer immune memory on account of their modulated expression of immune regulatory molecules. It is also believed that systemic dendritic cells may become activated after administration of the immunogenic formulation. In addition, it is believed that both NK cells and T cells, potent cancer killers with complementary expertise, are also activated.

Without being bound by theory, it is also believed that it is beneficial to use the patient's own hematopoietic cancer cells to generate the immunogenic formulation (as opposed to using an exogenous source of cancer cells) since using the patient's own cancer cells allow the virus to modulate the expression of endogenous immune regulatory molecules and thereby recruit the patient's immune system to target antigenic epitopes characteristic of the patient's own hematopoietic cancer cells. It is believed that the characteristic antigenic epitopes result in an immune response tailored to the patient's antigenic epitopes presented on the specific cancer cells.

The patient's hematopoietic cancer cells may be isolated (for example by leukopheresis in the case of leukocytes), or non-isolated (for example leukocytes in whole blood). The patient's hematopoietic cancer cells are exposed to sufficient numbers of viral particles so that sufficient numbers of the hematopoietic cancer cells increase in immunogenicity to generate an immune response in the patient when the infected cells are administered to the patient. The hematopoietic cancer cells must be intact when infected with the virus. However, the hematopoietic cancer cells may be intact or partially destroyed when the immunogenic formulation is administered to the patient. The hematopoietic cancer cells may be partially destroyed by, for example, fixing, such as by freeze thaw or formaldehyde or by any other method known to a skilled person to fix cells.

In human patients, a sufficient number of infected cells may be, for example, at least 100 infected hematopoietic cancer cells. In one example, the sufficient number may be at least 1,000 infected hematopoietic cancer cells. In another example, the sufficient number may be at least 10,000 infected hematopoietic cancer cells. In still another example, the sufficient number may be at least 100,000 infected hematopoietic cancer cells. In still another example, the sufficient number may be at least 1,000,000 infected hematopoietic cancer cells. In yet another example, the sufficient number may be at least 10,000,000 infected hematopoietic cancer cells.

In murine patients, a sufficient number of infected cells may be, for example, at least 100 infected hematopoietic cancer cells. In one example, the sufficient number may be at least 10,000 infected hematopoietic cancer cells. In still another example, the sufficient number may be at least 100,000 infected hematopoietic cancer cells.

To generate the infected hematopoietic cancer cells, as little as 1 viral particle per 100 hematopoietic cancer cells may be used to infect the hematopoietic cancer cells, if the virus is able to replicate and spread from cell to cell. Larger numbers of viral particles per 100 hematopoietic cancer cells may also be used to generate the infected hematopoietic cancer cells, for example if the virus is unable to replicate and spread from cell to cell. For example, the ratio of viral particles to hematopoietic cancer cells may be 1:1, 10:1, 1000:1, 10,000:1, or even greater.

As used herein, the term "ex vivo" means outside of the patient's body. An ex vivo viral infection of the patient's hematopoietic cancer cells could, for example, include: viral infection of isolated hematopoietic cancer cells being cultured in a lab, viral infection of a sample of the patient's whole blood in a vial, viral infection of a biopsied sample obtained from the patient, viral infection of hematopoietic cancer cells obtained by apheresis of whole blood, or viral infection of hematopoietic cancer cells obtained by purification and sorting from whole blood. An ex vivo viral infection may include expansion of the infected cancer cells before being administered to the patient.

Immune regulatory molecules are molecules which modulate the activity of the patient's immune system. The endogenous immune regulatory molecules whose expression may be modulated by the virus to increase the immunogenicity of the infected hematopoietic cancer cells may include, for example: cytokines released by the cell, immunomodulatory markers expressed on the cell surface, immunomodulatory molecules released by the cell, or any combination thereof.

The cytokines released by the cell may include, for example: CCL5, CCL4, IL-6, interferon-γ, IL-2, IL-12, IL-15, or any combination thereof. Immunomodulatory markers expressed on the cell surface may be immunostimulatory. Immunostimulatory markers which are expressed on the cell surface may include, for example: CD40, OX40 ligand (OX40L, also known as gp34, a member of the TNF superfamily), Inducible costimulator-ligand (ICOS-L), OX40 (CD 134), ICOS (CD278), CD137, CD137 ligand, CD40 ligand, CD28, calreticulin or any combination thereof. Increasing the expression of immunostimulatory markers increase the immunogenicity of the infected hematopoietic cancer cells. Immunomodulatory markers expressed on the cell surface may be immunosuppressant. Immunosuppressant markers which are expressed on the cell surface may include, for example: CD95, FAS, FAS ligand or any combination thereof. Decreasing the expression of immunosuppressant markers increase the immunogenicity of the infected hematopoietic cancer cells. Immunomodulatory molecules released by the cell can also include proteins like calreticulin.

The patient's hematopoietic cancer cells should be viable at the time of infection so that viral gene translation can occur so that the virus can modulate the expression of the plurality of immune regulatory molecules. Replication of viral particles may occur, but is not required.

As the expression of the plurality of endogenous immune regulatory molecules is modulated, the immunogenicity of the infected hematopoietic cancer cells increases. The infected hematopoietic cancer cells may have sufficient immunogenicity to be considered an immunogenic formulation after, for example, a single gene replication cycle of the virus. With some viruses, the infected hematopoietic cancer cells may have sufficient immunogenicity to be considered an immunogenic formulation 4 to 6 hours after infection with the virus.

To determine if a formulation is an immunogenic formulation, the formulation may be tested in a bio-response assay. For example, the formulation may be administered to a test subject and, after a period of time, the presence of immune activating cytokines in the test subject above a predetermined baseline level indicates that the formulation is an immunogenic formulation. In another example, the formulation may be administered to a test subject and, after a period of time, the presence of lymphocytes (as measured using a lymphocyte proliferation assay) above a predetermined baseline indicates that the formulation is an immunogenic formulation. Alternatively, a formulation may be determined to be an immunogenic formulation after being administered to the patient. For example, the formulation may be administered to the patient and after a period of time, the presence of immune activating cytokines in the patient above a predetermined baseline level indicates that the formulation was an immunogenic formulation. In another example, the formulation may be administered to the patient and the formulation would be determined to be an immunogenic formulation if the number of cancer cells present in the patient's body decreased after administration. This could be measured, for example, by reduction of PCR transcripts characteristic of the cancer; or could be suggested, for example, by a lack of cancer relapse. A formulation is considered to be an immunogenic formulation so long as one test indicates that the formulation is an immunogenic formulation.

For convenience, the virus may include a reporter gene to indicate when viral gene replication has begun. For example, the virus may include a gene that encodes green fluorescent protein (GFP). When hematopoietic cancer cells are infected with such a virus and become fluorescent, it suggests that gene replication has begun and the formulation is an immunogenic formulation. Alternatively, an aliquot of cancer cells could be tested before and after viral infection to measure a change in immune regulatory molecules present in the aliquot. When the change is greater than a predetermined baseline level, it suggests that the formulation is an immunogenic formulation.

The infected hematopoietic cancer cells may be incubated for a period of time to allow the virus to modulate the expression of the plurality of endogenous immune regulatory molecules to increase the immunogenicity of the infected hematopoietic cancer cells. Although a portion of the infected cells in the formulation may undergo cell lysis (that is, rupturing of the cell wall or membrane), it is desirable that a portion of the infected cells in the formulation be intact. Intact cells may include cells that have undergone programmed cell death (that is, apoptotic cells) but have not ruptured. With some viruses, hematopoietic cancer cells may rupture 30 to 35 hours after infection with the virus and, as a result of the decreased number of intact, infected cells, result in an immunogenic formulation of reduced immunogenicity.

It is desirable that the portion of intact infected cells in the formulation includes at least 100 infected hematopoietic cancer cells per dose. In one example, the portion of intact infected cells in the formulation includes at least 1,000 infected hematopoietic cancer cells per dose. In another example, the portion of intact infected cells in the formulation includes at least 10,000 infected hematopoietic cancer cells per dose. In still another example, the portion of intact infected cells in the formulation includes at least 100,000 infected hematopoietic cancer cells per dose. In another example, the portion of intact infected cells in the formulation includes at least 1,000,000 infected hematopoietic cancer cells per dose. In yet another example, the sufficient number may be at least 10,000,000 infected hematopoietic cancer cells.

An administered immunogenic formulation according to the present disclosure may contain a combination of infected, intact cells as well as necrotic material. The intact cells may include apoptotic cells.

Using an immunogenic formulation according to the present disclosure after remission induction and recovery may reduce residual disease since the immunogenic formulation may induce long-term protection against a leukemic burden. For example, therapy using an immunogenic formulation according to the present disclosure may induce an on-going immune surveillance of the leukemic stem cell and progeny—reducing the potential for relapse. It is contemplated that the immunogenic formulation may be used for patients in remission or not in remission. It is also contemplated that the immunogenic formulation may be used before, during or after conventional treatment. It is contemplated that the immunogenic formulation may be used as a stand-alone therapy without the use of other treatment.

Virus.

Viruses that may be used to generate the immunogenic formulation are viruses that modulate the expression of a plurality of endogenous immune regulatory molecules to increase the immunogenicity of the infected hematopoietic cancer cells. The viruses may have a natural ability to modulate the expression of the endogenous immune regulatory molecules, or the viruses may be modified to have an ability to modulate the expression of the endogenous immune regulatory molecules. The viruses may, for example, simultaneously induce the expression of a range of tumor-associated antigens, an enriched concentration of cell surface co-stimulatory molecules and a cytokine secretion profile; which may be conducive to the induction of broad tumor specific cytotoxic T-cell activation and expansion. The viruses may be incapable of integrating into the genome of the infected cell.

Examples of viruses which may be used to generate the immunogenic formulation include viruses of the Rhabdoviridae family, viruses of the Togaviridae family, viruses of the Leporipoxvirus family, viruses of the Reoviridae family, viruses of the Paramyxovirus family, viruses of the Picornavirus family, viruses of the Herpesviridae family, and viruses of the Adenoviridae family.

Specific examples of viruses of the Rhabdoviridae family that induce the expression of a plurality of endogenous immune regulatory molecules to increase the immunogenicity of infected hematopoietic cancer cells include: vesicular stomatitis virus (VSV), maraba virus, carajas virus, and chandipura virus. Examples of vesicular stomatitis virus may include the Indiana strain and the New Jersey strain.

Specific examples of viruses of the Togaviridae family that induce the expression of a plurality of endogenous immune regulatory molecules to increase the immunogenicity of infected hematopoietic cancer cells include: semliki forest virus.

Specific examples of viruses of the Leporipoxvirus family that induce the expression of a plurality of endogenous immune regulatory molecules to increase the immunogenicity of infected hematopoietic cancer cells include: Myxoma virus.

Specific examples of viruses of the Reoviridae family that induce the expression of a plurality of endogenous immune regulatory molecules to increase the immunogenicity of infected hematopoietic cancer cells include: Reovirus virus.

Specific examples of viruses of the Paramyxovirus family that induce the expression of a plurality of endogenous immune regulatory molecules to increase the immunogenicity of infected hematopoietic cancer cells include: Measles virus and Mumps virus.

Specific examples of viruses of the Picornavirus family that induce the expression of a plurality of endogenous immune regulatory molecules to increase the immunogenicity of infected hematopoietic cancer cells include: Coxsackievirus A21 virus.

Wild type viruses may be modified to include beneficial characteristics. Examples of beneficial characteristics may include, for example: a reduced ability to infect non-cancerous cells; a reduced ability to spread to other cells; induction of at least one endogenous immune regulatory molecule that is not otherwise expressed; increased expression of at least one endogenous immune regulatory molecule; or any combination thereof.

Wild type viruses may be modified to induce expression of molecules that are not otherwise expressed, or to increase expression of molecules which are already expressed, by the addition of genes which, for example, encode activator proteins to increase the rate of transcription of the immune regulatory molecule.

Wild type viruses may be modified to reduce their ability to infect non-cancerous cells by making the modified virus more sensitive to interferons, which are proteins made and released by infected cells in response to pathogens such as viruses. The interferons interfere with viral replication within host cells. The production of interferons is often reduced in cancerous cells in comparison to non-cancerous cells. Therefore, viruses that are sensitive to interferons will have a reduced ability to infect non-cancerous cells (which produce interferons) in comparison to their ability to infect cancerous cells (where production of interferons is reduced). Wild type viruses may be modified to make the virus more sensitive to interferon by, for example: preventing the virus from blocking interferon response in infected cells; or preventing the virus from blocking nuclear/cytoplasmic transport of host mRNAs and thereby allowing the host cell to propagate an interferon response.

Wild type viruses having a molecule mediated cell entry may be modified to reduce their ability to spread to other cells by reducing their ability to enter a cell using the molecule mediated entry. One example of such a mediated entry is glycoprotein (G protein) mediated cell entry. The G protein mediates virus attachment to a cell where it is subsequently endocytosed. The G protein then mediates fusion of the viral envelope with the endosomal membrane. Mutations to or deletions of the DNA encoding the G protein may thereby reduce the ability of modified viruses to spread to other cells in comparison to the ability of wild-type viruses. Another example of a molecule mediated entry is lipoprotein mediated entry.

Examples of specific mutations in the Maraba virus that provide beneficial characteristics include mutations: L123W and Q242R in the Maraba sequence of the M and G proteins, respectively. The resulting modified virus is termed the "MG1" virus and was first reported in *Molecular Therapy* (2010) 18:8, 1440-1449. Examples of specific mutations in the vesicular stomatitis Indiana virus that provide beneficial characteristics include mutations: L123W and H242R in the VSV sequence of the M and L proteins. Other examples of modified wild type viruses which may be used to generate an immunogenic formulation according to the present disclosure are disclosed in Molecular Therapy (2010) 18:8, 1440-1449.

One example of a modified virus is MG1, a rhabdovirus with interferon dependent and independent attenuating deletions in the matrix and glycoprotein proteins respectively. Compared to uninfected cells, MG1 infected L1210 cells have marked increase in a number of potent cell surface co-stimulatory molecules including CD40 and Ox40 ligand in addition to a significant increase in chemotactic cytokines including CCL5, CCL4, and IL-6 (FIGS. 1*a* and 1*b*). FIG. 1*a* is a graph illustrating a cytokine array or profile of L1210 cells infected with MG1 virus. The relative concentration to uninfected L1210 cells is shown as a function of the different cytokines of the cytokine array. FIG. 1*b* is a graph showing flow cytometry data illustrating the increase in CD40+ expression after viral infection of L1210 cell with MG1.

Another example of a modified virus is rhabdovirus Vesicular Stomatitis Virus Δ51 (VSV-d51), which is modified to delete the $51^{st}$ amino acid in the M protein. This virus is an RNA virus sensitive to the antiviral effects of type I interferons. Still another example of a modified virus is VSV-d51 which was also G-protein deleted (VSVd51ΔG).

Preparation.

Immunogenic formulations according to the present disclosure are prepared by exposing, ex vivo, the patient's hematopoietic cancer cells to a virus that modulates the expression of a plurality of endogenous immune regulatory molecules to increase the immunogenicity of the infected hematopoietic cancer cells. As previously discussed, the infected hematopoietic cancer cells may have sufficient immunogenicity to be considered an immunogenic formulation after, for example, a single gene replication cycle of the virus. With some viruses, the infected hematopoietic cancer cells may have sufficient immunogenicity to be considered an immunogenic formulation 4 to 6 hours after infection with the virus. In some examples, the hematopoietic cancer cells are incubated with the virus for 18 hours. The hematopoietic cancer cells may be incubated for less than a specific time, for example less than 35 hours, in order to reduce the amount of cell lysis. The immunogenic formulation is administered to the patient while the immunogenic formulation still includes a sufficient numbers of intact, infected cancer cells to induce an immune response.

The immunogenic formulations may be gamma irradiated to stop the hematopoietic cancer cells from propagating, thereby reducing the possibility that uninfected hematopoietic cancer cells in the formulation might propagate when administered to the patient. In some examples, the immunogenic formulation is not exposed to gamma irradiation.

Administration.

The appropriate amount of immunogenic formulation to be administered to the patient may be determined by a skilled clinician on a case-by-base basis. In some examples, the appropriate amount to be administered to a human patient is a daily dosage of immunogenic formulation containing from about $1\times10^4$ to about $1\times10^8$ intact, infected hematopoietic cancer cells. In specific examples, the appropriate amount to be administered is a daily dosage of the formulation containing about $1\times10^5$ to about $1\times10^7$ intact, infected hematopoietic cancer cells.

The daily dosage of the immunogenic formulation may be administered to the patient in multiple administrations over the course of a single twenty-four hour period, in which a portion of the daily dosage is administered at each administration. Alternatively, the daily dosage may be administered in a single dose.

The daily dose may be administered once or more than once. For example, multiple daily dosages of the immunogenic formulation may be administered to the patient. In some examples, two, three, four, five, six, seven, eight, nine, ten, or more daily dosages are administered to the patient. The multiple daily dosages of the immunogenic formulation may be administered to the patient over the course of many days. For example, a patient may be administered a daily dose every day, every other day, every three days, every four days, every five days, every six days, every seven days, every eight days, every nine days, every ten days, every two weeks, every three weeks, every month, every two months, every six months, or any time between any of the listed time periods. In other examples, a patient may be administered a daily dose at a schedule determined by a skilled clinician in view of the patient's immune profile. The schedule may be, for example, an irregular schedule.

For example, a single dose may be administered to the patient with one, two, three, or more than three, booster dosages subsequently administered weeks, months or years after the initial dose.

The immunogenic formulation may be administered though any conventional route of administration. For example the formulation may be administered intravenously, intratumorally, intraperitoneally, intravesicularly (kidneys), subcutaneously or intramuscularly. When the cancer is other than a solid tumor (e.g. leukemia) the formulation is not administered intratumorally but may be instead administered by the other routes given above, for example intravenously.

Cancers.

Hematopoietic cancers are cancers of hematopoietic stem cell derived tissues. Hematopoietic cancers may be solid tumors, for example lymphomas, or liquid tumors, for example leukemias. Leukemias may include, for example, acute myelogenous leukemia (AML), acute lymphoblastic leukemia (ALL), chronic lymphocytic leukemia (small lymphocytic lymphoma when leukemic cells are absent), chronic myelogenous leukemia, acute monocytic leukemia. Lymphomas may include, for example, Hodgkin's lymphoma (with 4 subtypes) and non-Hodgkin's lymphoma.

Hematopoietic cells are subgrouped broadly into myeloid cells (erythrocytes, thrombocytes, neutrophils, monocytes and macrophages, eosinophils, basophils, mast cells) and lymphoid cells (B-cells, various types of T lymphocyte cells, natural killer cells).

The expression of endogenous immune regulatory molecules may be modulated in the hematopoietic cancer cells to recruit the patient's immune system to target antigenic epitopes characteristic of the patient's own hematopoietic cancer cells.

Kits.

The immunogenic formulation may be generated using a kit that includes a container previously prepared to contain a virus that modulates the expression of a plurality of endogenous immune regulatory molecules to increase the immunogenicity of infected hematopoietic cancer cells. The container may be, for example, a vial and the immunogenic formulation is generated by adding an aliquot of the patient's hematopoietic cancer cells to the vial. The added hematopoietic cancer cells become infected with the virus and generate the immunogenic formulation. The aliquot of the patient's hematopoietic cancer cells may be, for example: an aliquot of isolated hematopoietic cancer cells, an aliquot of whole blood, or a portion of biopsied tissue.

In one example, the kit may include a vial which previously prepared to contain a virus as described above that was further modified to include a gene that encodes for green fluorescent protein. When the hematopoietic cancers added to the vial became fluorescent, it would suggest that gene replication has begun and the aliquot is an immunogenic formulation according to the present disclosure.

In another example, a kit may include: a first vial which previously prepared to contain a virus as described above which did not include a gene that encodes for green fluorescent protein, and a second vial which was previously prepared to contain a virus that includes a gene that encodes for green fluorescent protein. When the hematopoietic cancers added to the second vial became fluorescent, it would suggest that gene replication has begun in the aliquot in the first vial, and that the aliquot in the first vial is an immunogenic formulation according to the present disclosure.

Methods

Mice.

DBA/2, C57BL/6, athymic mice and B6D2F1 hybrid mice (all 6 weeks of age) were purchased from Charles River Laboratories (Wilmington, Mass.) and housed in a biosafety unit at the University of Ottawa, accredited by the Canadian Council on Animal Care (CCAC). Institutional guidelines and review board for animal care (The Animal Care and Veterinary Service of the University of Ottawa) approved all animal studies.

Tumor Cells.

L1210 and EL4 murine lymphoblastic cell lines, from ATCC (Manassas Va.), were maintained in suspension culture, Dulbecco's modified Eagle's medium-high glucose (DMEM) (HyClone, Logan, Utah), with 10% fetal calf serum (FCS) (CanSera, Etobicoke, ON) at 37° C. and 5% $CO_2$. Cells were routinely split every 2-4 days to maintain concentration between $0.5-1.0\times10^6$ cells/mL. The Jurkat human acute T-cell lymphoblastic leukemia cell line, from ATCC, the human acute immunoblastic B-cell line OCI-Ly-18, gift of Dr. Hans Messner (Ontario Cancer Institute), and the human acute T-cell lymphoblastic cell line A301, gift from Dr. Thomas Folks of the AIDS Research and Reference Reagent Program, Division of AIDS, NIAID, NIH, were maintained in similar culture conditions. The Vero cell line, from ATCC, was maintained as adherent cell cultures in DMEM and 10% FCS. Vero cells were used for virus propagation, detection or enumeration of infectious viral particles and for viral-neutralization antibody assays. T-RexTM-293 cells (Invitrogen, Carlsbad, Calif.) were used for manufacturing of VSVd51ΔG virus. L1210 (ALL cell line), EL4 (NK-T cell line), Vero, Jurkat, Ly-8 and A.301 cells were maintained in media (Dulbecco's modified Eagle's medium-high glucose (HyClone, Logan, Utah) supplemented with 10% fetal calf serum (CanSera, Etobicoke, Canada) at 37° C. with 5% $CO_2$. For apoptotic cell preparations, uninfected L1210 cells were washed in phosphate buffered saline (PBS) and plated at $2\times10^6$/mL (10 mL/150×25 mm plate) and treated with ultraviolet c irradiation (UVC) at 500 mJ/cm² (Spectrolinker—Spectronics—Westbury, N.Y.), then re-plated and incubated in fresh media for 4 hours prior to re-collection. Cells were then washed and re-suspended in PBS at $1\times10^7$ cells/mL. For necrotic cell preparations, a French press hydraulic applied the minimum pressure to ensure cell membrane disruption (1500 PSI) to washed uninfected L1210 cells at $1\times10^7$ cells/mL. For tumor challenges, cells were washed in PBS and $10^6$ cell/100 μL immediately injected via the tail vein or at additional specified concentrations. Vero cells were used for viral titer measurements and viral-neutralization antibody assays.

Virus.

Figure 2:
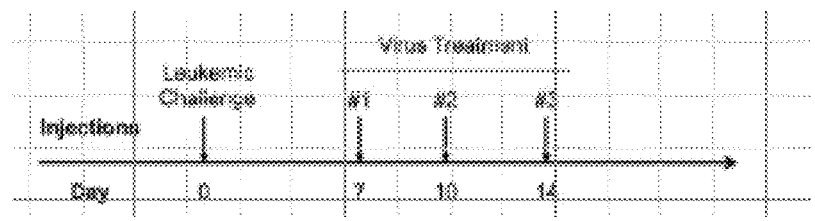
FIG. 2 is graph illustrating an exemplary treatment schedule for an immunogenic formulation according to the present disclosure.

The single-stranded negative sense RNA maraba virus MG1, was originally provided by Stojdl (Ottawa, ON), see *Molecular Therapy* (2010) 18:8, 1440-1449. MG1 is a rhabdovirus with interferon dependent and independent attenuating deletions in the matrix and glycoprotein proteins respectively. MG1 has been shown to exhibit a 1000 fold increase in its therapeutic index as a result of these double mutations. The engineered rhabdovirus Vesicular Stomatitis Virus Δ51 (VSV-d51) is a similar RNA virus sensitive to the antiviral effects of type I interferons. VSV-d51 and MG1 were propagated in Vero cells. The multi-attenuated VSVd51 G-protein deleted virus (VSVd51ΔG) was propagated in T-Rex™-293 cells using Blasticidin and Zeocin™ according to manufacturer's recommendations (Invitrogen—Carlsbad, Calif.). Virus purification was performed as previously described, for example by Brown, C W et al. in *J. Virol* (2009) 83: 552-561. Virus expressing the enhanced green fluorescence protein (eGFP) was used for immunogenic formulation and control preparations to permit pre-injection analysis of infected cells by flow cytometry and fluorescence microscopy. Ultraviolet radiation was used to inactivate virus when required for specific immunogenic formulation preparations. When MG1 was used to treat established L1210 leukemia, mice were given a predetermined maximum tolerable dose (MTD) of $1\times10^8$ plaque forming units (pfu) MG1 by tail vein every 3 days×3 (FIG. 2). Enumeration of virus particles was performed as described in Breitbach C J, Paterson J M, Lemay C G, Falls T J, McGuire A, Parato K a, et al. "Targeted inflammation during oncolytic virus therapy severely compromises tumor blood flow", Molecular Therapy: the Journal of the American Society of Gene Therapy (2007) 15:1686-93. Suspension cultures of human and murine leukemic cells were infected by adding virus preparations directly to culture (at $1\times10^6$ cells/mL), at a multiplicity of infection (MOI) of 0.1.

The toll-like receptor (TLR) 3 agonist polyinosinic-polycytidylic acid (poly I:C) and TLR4 agonist lipopolysaccharide (LPS) were purchased from Sigma Aldrich (St. Louis, Mo.). Propidium iodide, 7-AAD viability-staining solutions and Annexin V Apoptosis Detection Kit APC were obtained from eBioscience. (San Diego, Calif.).

Immunogenic Formulation and Control Formulation.

Exemplary immunogenic formulations according to the present disclosure were prepared by infecting L1210 or EL4 cells with virus at $1 \times 10^6$ cells/mL at a multiplicity of infection (MOI) of 10. After 18 hours of incubation in media at 37° C., samples were analyzed by flow cytometry and fluorescence microscopy, then washed and re-suspended in PBS at $1 \times 10^7$ cells/mL. The exemplary formulations were gamma-irradiated ($\gamma$-IR) at 30 Gy immediately prior to the injection of 100 µL of the preparation—administered via tail vein. Control experiments used uninfected leukemia cells and injected alone, co-injected with MG1 (MOI 10) in a separate syringe or mixed with MG1 at MOI of 10, at room temperature 60 minutes prior to administration. In other experiments, immunogenic formulations according to the present disclosure were prepared by infecting L1210 cells with virus and then subjecting the infected virus to 3 cycles of freezing on dry ice and thawing in a 37° C. water bath, or to fixing in 1% (final) paraformaldehyde (PFA) before $\gamma$-IR.

In other control experiments, control formulations were prepared using toll-like receptor (TLR) agonists instead of virus. Specifically, standard murine doses of either 150 µg/100 µL poly I:C or 17 µg/100 µL LPS were added to L1210 cells prior to $\gamma$-IR and injection; or 150 µg/$10^6$ cells poly I:C and/or 17 µg/$10^6$ cells LPS were add to cultures of L1210 cells for 18 hours prior to washing and $\gamma$-IR.

In yet other control experiments, apoptotic leukemia cells were prepared from uninfected L1210 cell cultures. The cells were pelleted by centrifugation, washed once and resuspended in PBS at $2 \times 10^6$/mL. Ten mL of cell suspension was placed in a 150×25 mm plate and exposed to 500 mJ/cm$^2$ UVC. Cells were then pelleted, resuspended in fresh media and incubated at 37° C. for 4 hours prior to preparation for use. Necrotic leukemia cells were prepared by pressure disruption (1500 PSI) of washed uninfected L1210 cells at $1 \times 10^7$ cells/mL in a French hydraulic press (AMINCO J5-598A, Newport Scientific—Jessup, Md.).

Figure 3A:
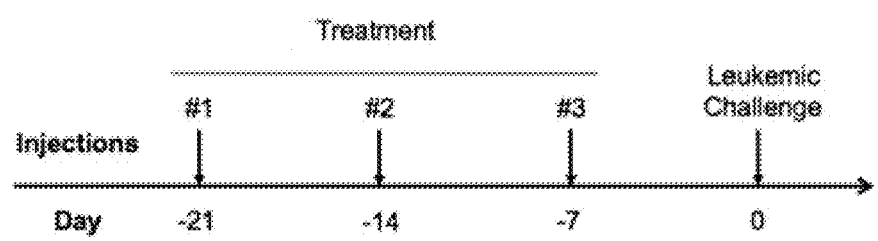
FIGS. 3a to 3e are graphs illustrating results from pre-treatment with an immunogenic formulation according to the present disclosure.

With mice, formulations were administered once weekly ×3, followed one week later by a leukemic challenge typically at a dose of $1 \times 10^6$ cells/100 µL, as illustrated in FIG. 3a. Mice were euthanized upon the development of predetermined signs of illness including typical leukemic end-points, such as hind-leg paralysis, focal tumor development, significant weight loss or respiratory distress.

Adoptive Cell Transfer.

A pooled splenocyte single cell suspension was prepared under sterile conditions according to manufacturer's recommendations (gentleMACS Dissociator—Miltenyi Biotec, Auburn, Calif.) from 17 donor mice previously treated with the immunogenic formulation. Each of the 8 recipient mice equally received a total of $15 \times 10^7$ donor splenocytes in PBS via tail vein and intraperitoneal routes.

Flow Cytometry and Cytokine Multiplex Array.

Preparations were analyzed by flow cytometry prior to final preparation and injection. Cell viability for the immunogenic formulation and infected cell analyses was assessed by propidium iodide and 7-AAD viability-staining solutions (eBioscience—San Diego, Calif.). Early apoptosis and late stage apoptosis/necrosis was assessed using the Annexin V apoptosis detection kit APC and 7-AAD (eBioscience). Ox-40Ligand-PE (eBioscience) and CD4O-PE (BD Bioscience—Franklin Lakes, N.J.) were optimized as per manufacturer's recommendations. The 32 cytokine array was performed using the Bio-Plex Pro™ Mouse Cytokine 9-Plex Assay #MD0-00000EL and Bio-Plex Pro™ Mouse Cytokine 23-plex Assay #M60-009RDPD (Bio-Rad—Hercules, Calif.). To prevent interference from L1210 cytokine secretion, L1210 cells were pre-incubated with brefeldin A (1 µL/$10^6$ cells BD GolgiPlug™—BD Biosciences) for 1 hour then washed 2× with PBS, followed by co-culture in media with immunogenic formulation-treated (5 bio-replicates with duplicates of each) or naive splenocytes at effector to target ratios of 0.2, 1.0, and 5.0, with target L1210 cells at $2 \times 10^6$ cells/mL. Supernatants were collected after 18 hours and analyzed using the magnetic bead multi-plex array kits using Bio-plex 200 (Bio-Rad)—based on xMAP® technology (Luminex—Austin, Tex.) according to manufacturers' recommendations. The same multiplex array system was also used to analyze uninfected and MG1 infected (MOI of 10, 18 hours incubation) L1210 cells, performed in triplicate.

Statistics.

Statistical analysis was performed using Prism 5 software.

Results

Pre-Treatment with Immunogenic Formulation Induces Protection from Leukemic Challenge.

A series of experiments were conducted to explore whether anti-tumor immunogenicity could be generated with a variety of immunogenic formulations prior to a leukemic challenge.

Figure 3B:
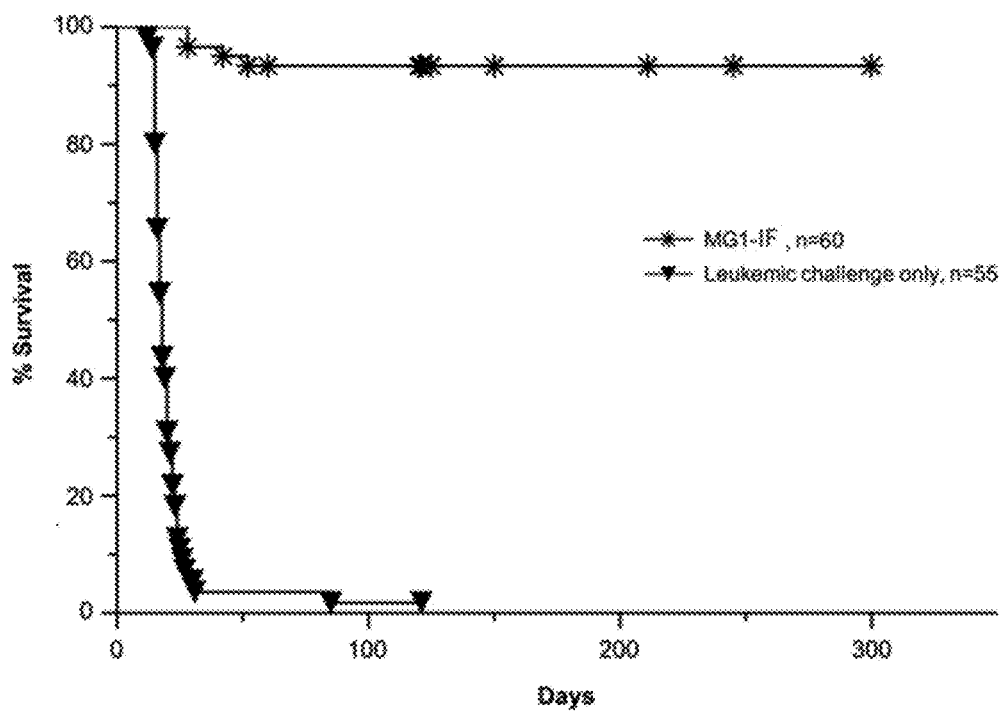

Mice that received immunogenic formulation made with MG1 demonstrated survival rate >90%, as opposed to untreated control mice, which reproducibly reached leukemic end-points, as illustrated in FIG. 3b which shows a survival curve of murine patients pre-treated with a specific exemplary immunogenic formulation made using MG1 and L1210 leukemia cells. Full leukemic rejection was considered to be 60 days leukemia-free survival, however, mice were typically observed for a minimum of 120 days.

Figure 3C:
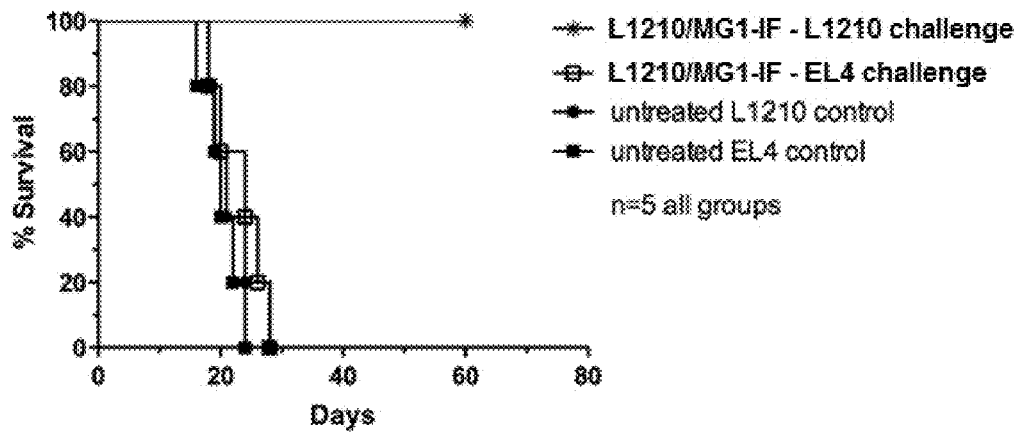
Figure 4:
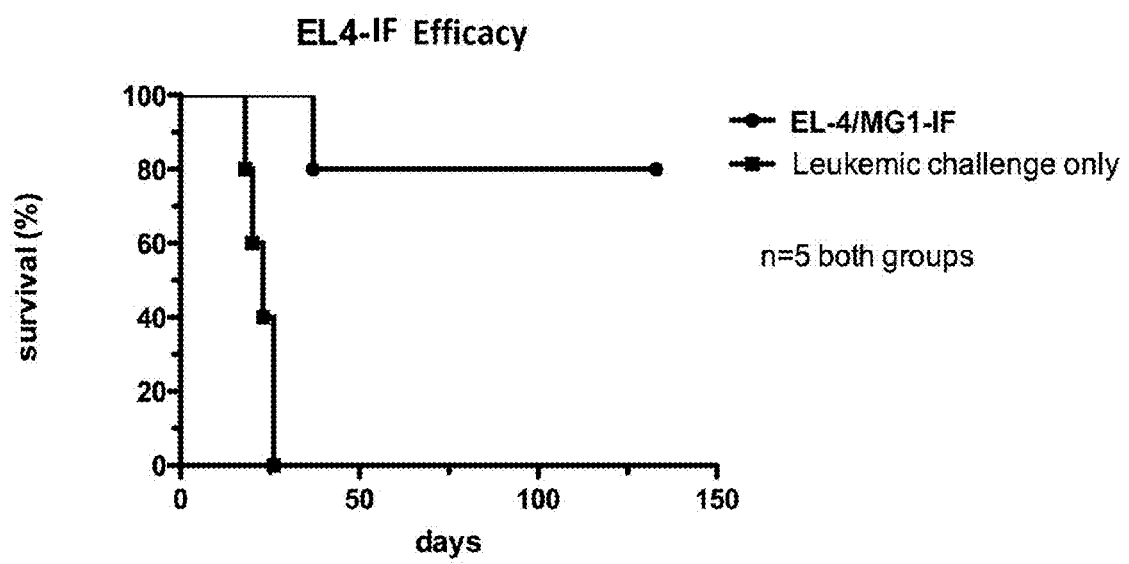
FIG. 4 is a graph illustrating the survival curves of another immunogenic formulation according to the present disclosure.

An alternate murine leukemia model was tested using EL4 leukemia cells, syngeneic to C57Bl/6 mice. The immunogenic formulation made with EL4 had similar efficacy as the formulation made with L1210 cells, as shown in FIG. 4 which illustrates the survival curves of an immunogenic formulation according to the present disclosure made with EL4. Interestingly however, the immunogenic formulation exhibited leukemia-specific protection. When B6D2F1 hybrid mice were administered the MG1 immunogenic formulation made with L1210 cells ("L1210/MG1-IF"), the cohort receiving L1210 leukemia was protected as usual, but the EL4 challenge group was uniformly unprotected, as illustrated in FIG. 3c which shows a survival curve for L1210-specific protection of B6D2F1 hybrid mice treated with the MG1 immunogenic formulation made with L1210 cells. This intriguing observation suggests that the immunogenic formulation induced anti-leukemic immune response is functionally restricted to the leukemic cell contained in the immunogenic formulation.

Figure 3D:
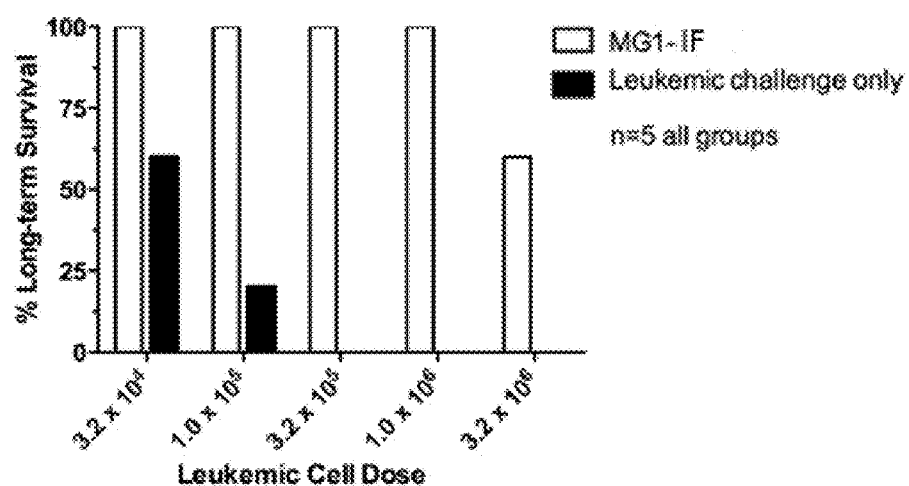

An immunogenic formulation may be considered to be a biologically significant vaccine or biotherapy when the recipient is protected against ≥1 logarithm of the 50% lethal dose (LD50) of the disease. The immunogenic formulation of the present disclosure protected mice from L1210 leukemia at least 1.5 logarithms above the LD50, as illustrated in FIG. 3d which shows a survival graph of treatment with an exemplary immunogenic formulation according to the present disclosure, showing protection at least 1.5 logarithms above the tumor LD50. This disease-free survival was consistently observed when the lethal leukemic challenge was administered 7 days following the immunogenic formulation series.

Figure 3E:
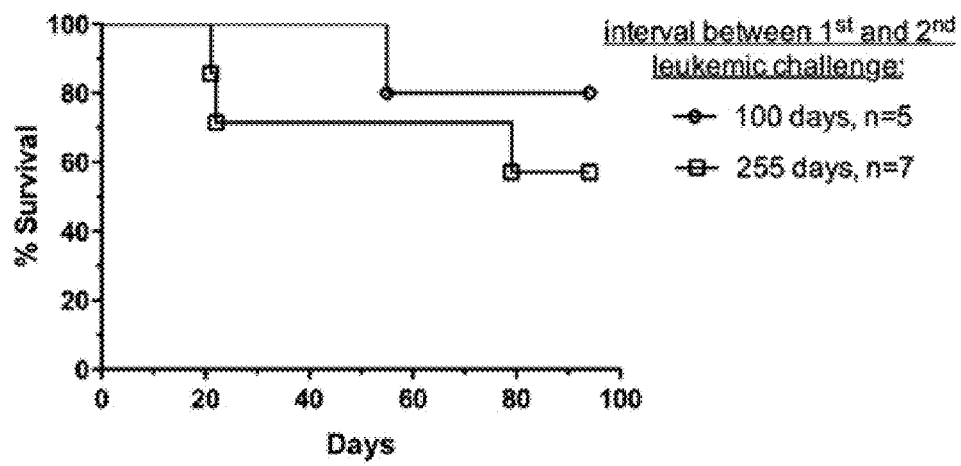

For clinical translation, the durability of such an immune response is particularly relevant. To test the strength and longevity of the immunogenic formulation induced immune response, mice that were protected by the initial leukemic challenge were administered a second lethal dose of leukemia. Survival rates of 60-80% were observed despite the prolonged period of time from initial vaccination as well as the advanced age of these mice, as illustrated in FIG. 3e which shows leukemia-free survival following a second tumor challenge administered after an initial challenge, (the control mice reached endpoints within 21 days).

Viable Leukemia Cells Infected with Virus.

Figure 5A:
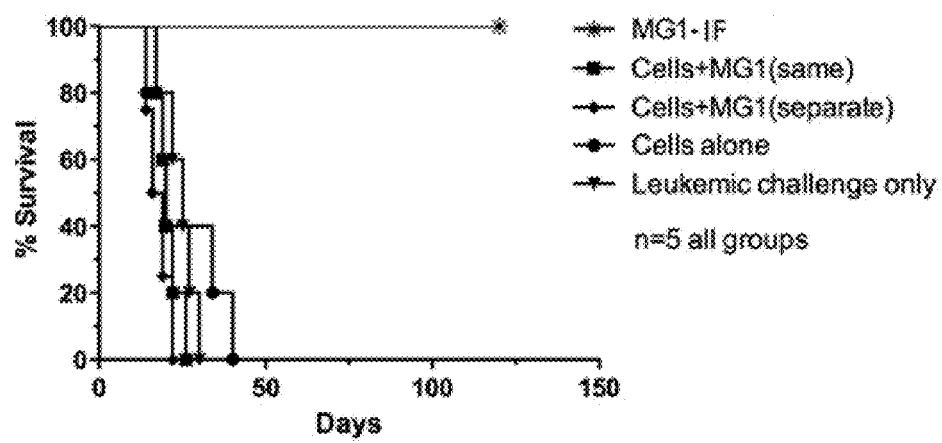
FIGS. 5a to 5d are graphs illustrating that viable leukemia cells infected with an exemplary virus result in an immunogenic formulation according to the present description.

In this study it was found that leukemia cells which were gamma irradiated to stop cellular division and to increase immunogenicity and which were subsequently supplemented with a variety of adjuvants were ineffective immunogenic formulations as mice were unable to reject leukemic challenge when pre-administered a formulation series of γ-IR leukemia cells alone, or γ-IR leukemia cells in combination with adjuvant live MG1 virus—either pre-mixed in the same injectate or administered separately, as illustrated in FIG. 5a which shows the survival curves for murine patients administered a series of gamma irradiated leukemic cells with adjuvant live MG1 virus either given as a separate injection or in the same injectate (mixed with cells for 1 hour prior to injection). Therefore, regardless of coincident immune stimulation from the virus acting as an adjuvant with the γ-IR leukemic cells, γ-IR leukemic cells were inadequate immunogens to induce leukemic protection. Similarly, when apoptotic cells, with or without MG1 virus, were used in an attempt to generate an immune response in mice, it was determined that they were insufficiently immunogenic to provide leukemic protection to the mice. In a similar manner, inflammatory necrotic cells, without or with MG1 virus, were insufficiently immunogenic to provide leukemic protection to the mice.

Virus acting as an adjuvant was not under-dosed compared to immunogenic formulations according to the present disclosure, since the quantity of adjuvant virus per injection ($10^7$ pfu) was greater than the total virus titer in exemplary the immunogenic formulation dose ($10^6$ pfu). Notably, the MG1 virus contains an immunogenic capsular glycoprotein that avidly binds to cell membranes permitting rapid viral adhesion to the cell surface of the host cell. Despite this close cell-virus association, mice that received the leukemic cells pre-mixed with MG1 virus (MOI 10—one hour prior to injection) did not develop an anti-tumor immune response sufficient for rejection of leukemic challenge.

Figure 5B:
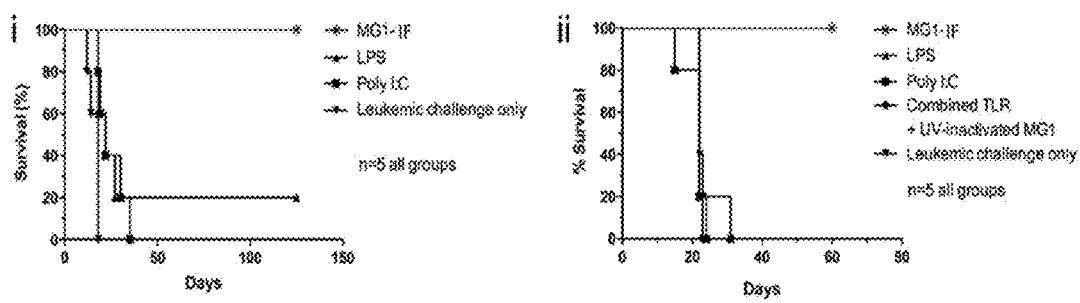

When standard laboratory immune stimulants were used as adjuvants for γ-IR leukemic cell, no leukemic protection was provided. For example, formulations comprised of γ-IR L1210 cells and poly I:C or LPS did not provide anti-tumor immune response sufficient for rejection of leukemic challenge, as illustrated in FIGS. 5b(i) and 5b(ii). FIG. 5b(i) shows the survival curves of the murine patients treated with an immunogenic formulation according to the present description. FIG. 5b(ii) shows reduced immunogenic capacity was induced in L1210 leukemic cells when stimulated (pre-incubated for 18 hours) with Poly I:C, LPS and UV-inactivated MG1 virus, as compared to the an immunogenic formulation according to the present disclosure. Similarly, when the same TLR agonists were incubated with L1210 cells for 18 hours prior to final formulation preparation (either separately or combined together in addition to UV-inactivated MG1), no protective effect was observed as opposed to the immunogenic formulation.

Figure 5C:
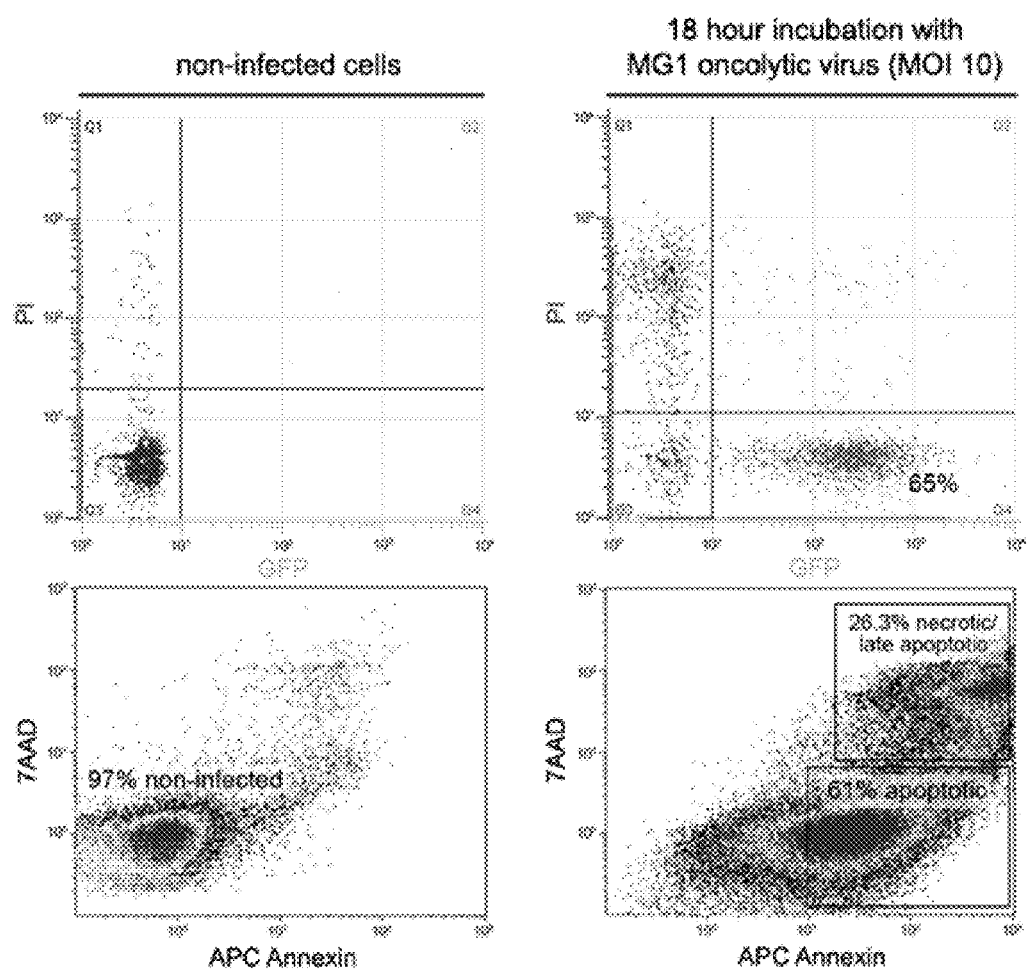
Figure 5D:
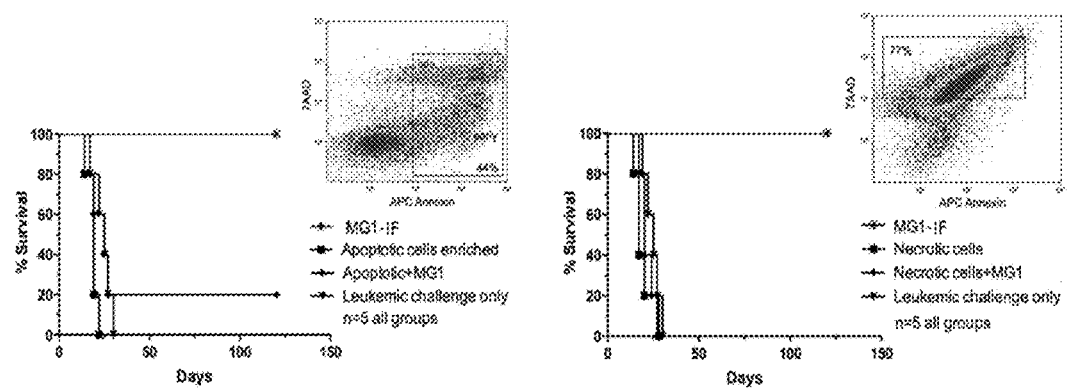

Following infection with a rhabdovirus virus, such as MG1, hematopoietic cancer cells will undergo apoptosis or eventually become necrotic from membrane rupture due to the brisk exocytosis of viral shedding or necroptosis. FIG. 5c shows flow cytometry data of an immunogenic formulation containing a mixture of infected cells, apoptotic cells and necrotic material with GFP expression (substantively infected cell), staining for annexin V alone (apoptotic cells) or annexin V and 7-AAD viability dye (late apoptotic/necrotic). As illustrated in FIG. 5c, apoptotic and necrotic cells accumulate when L1210 leukemia cells are incubated with virus. Both apoptotic and necrotic cells are immunomodulatory, with the potential for immune stimulation and dendritic cell activation. To examine the extent to which dying leukemic cells might contribute to the efficacy of an immunogenic formulation according to the present disclosure, without potential immunogenic interference from virus-induced cell transformation, uninfected L1210 cells were forced into apoptosis by UV-irradiation. Similarly, uninfected leukemic cells were pressure-disrupted, which produces an inflammatory necrotic cell that activates the innate immune system. No leukemic protection was observed when mice were administered formulations prepared using either one of these altered leukemia cells, with or without adjuvant MG1 virus, as illustrated in FIG. 5d which shows the survival curves with inlays of respective flow cytometry analysis. Taken together, these results indicate that immunogenic formulations according to the present disclosure require that the patient's hematopoietic cancer cells be viable at the time of infection so that the virus can induce the expression of the plurality of immune regulatory molecules.

Live-Attenuated Replication Incompetent Virus does not Impair Efficacy of the Immunogenic Formulation; Inactivated Virus Renders the Formulation Ineffectual.

Figure 6A:
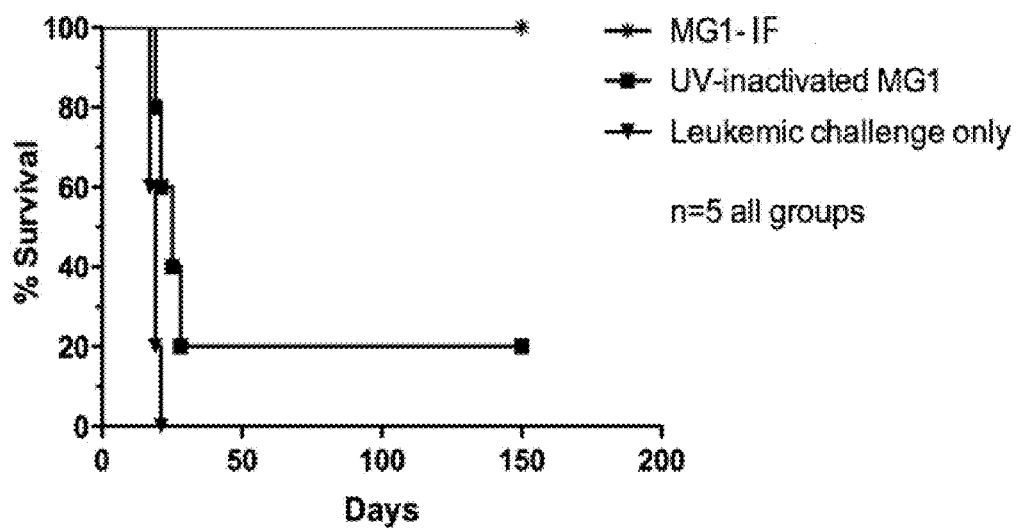
FIGS. 6a to 6d are graphs illustrating the anti-leukemic activity of various formulations.

Leukemic cells infected with UV-inactivated MG1 virus were not killed and did not express GFP. Although there may be a safety advantage in using UV-inactivated MG1 virus, formulations prepared by incubating leukemia cells for 18 hours with inactivated MG1 were found to be non-protective against subsequent leukemia challenge, as illustrated in FIG. 6a, which shows a survival curve of mice that received a formulation prepared using UV-inactivated MG1 virus.

Figure 6B:
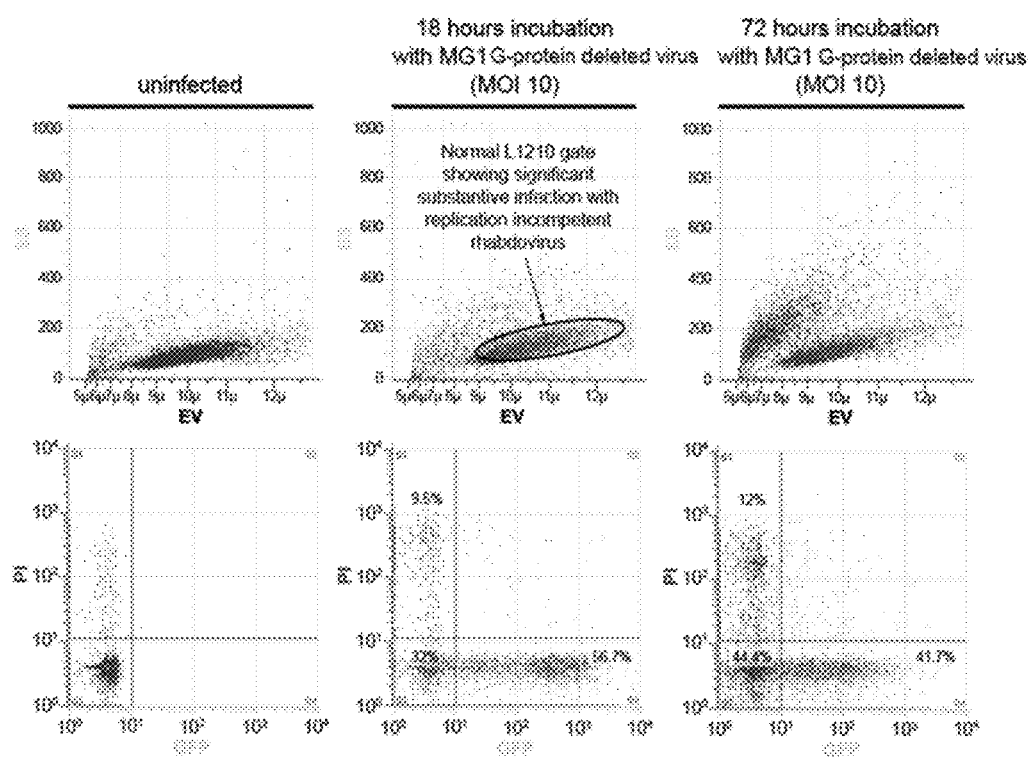
Figure 6C:
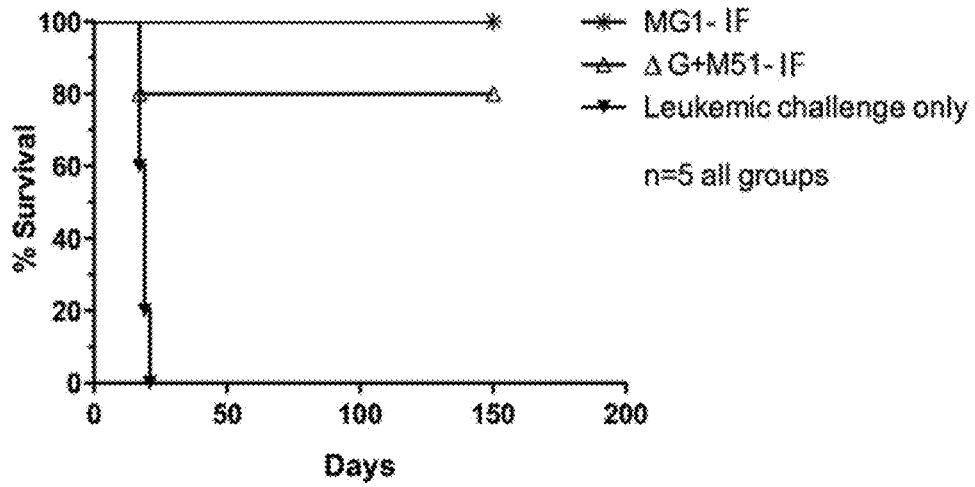
Figure 15A:
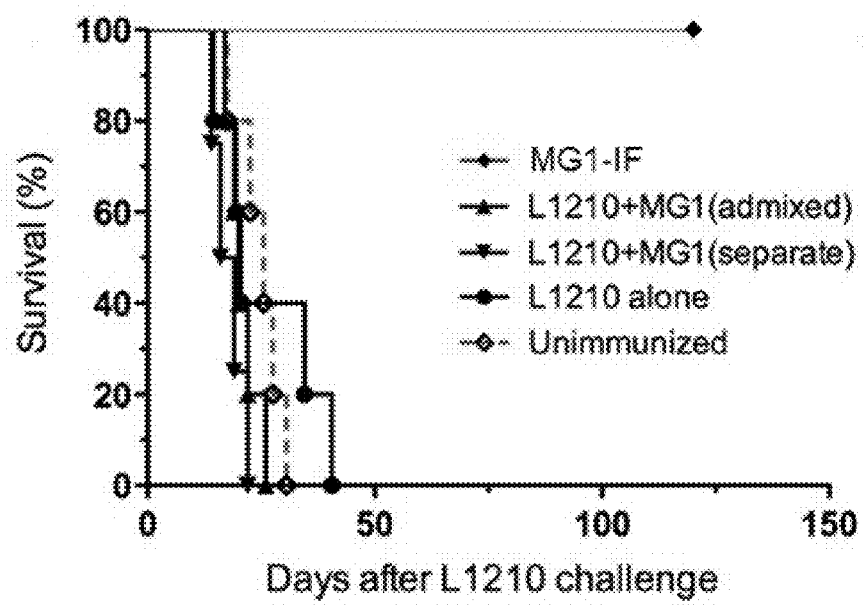
FIG. 15a is a graph illustrating a survival curve of DBA/2 mice administered an immunogenic formulation according to the present disclosure and challenged with L1201 leukemia cells, as compared to: untreated DBA/2 mice, DBA/2 mice administered a mixture of L1210 and virus, and DBA/2 mice administered L1210 and virus separately.
Figure 15B:
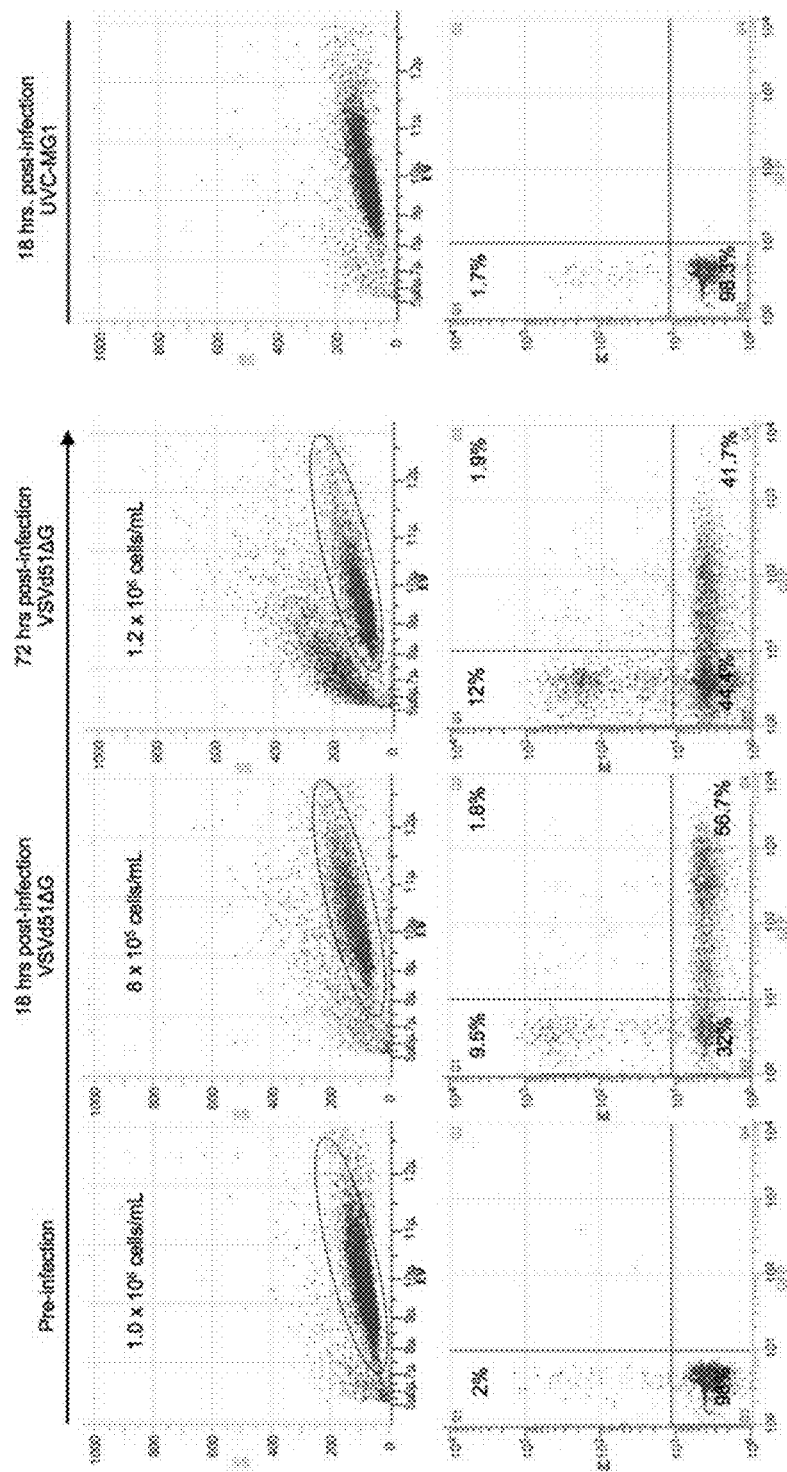
FIG. 15b are graphs of flow cytometry data of L12010 leukemia cells incubated with UV-inactivated MG1 virus, or attenuated VSVd51ΔG-eGFP virus. The oval region in the graphs indicate viable L1210 lymphoblasts.
Figure 15C:
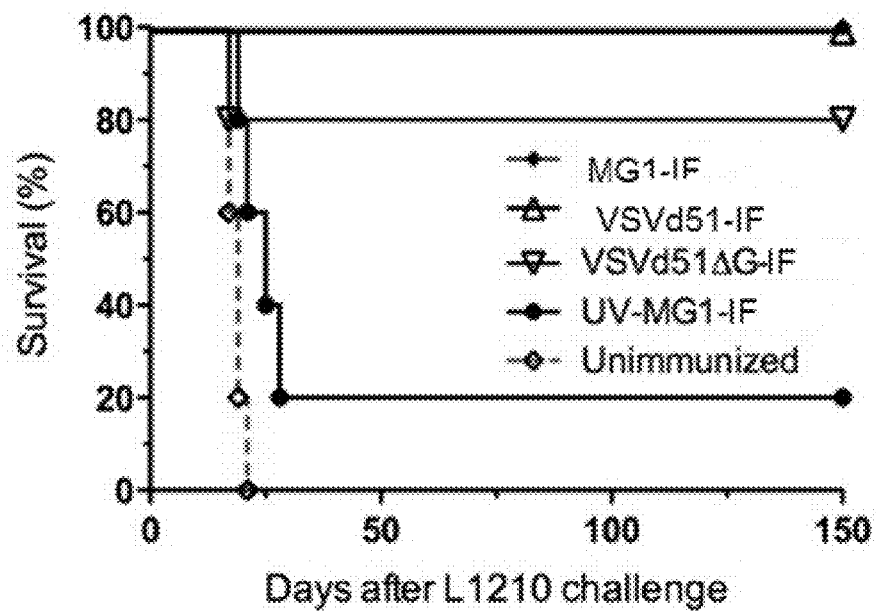
FIG. 15c is a graph illustrating a survival curve of DBA/2 mice administered different immunogenic formulations according to the present disclosure and challenged with L1210 leukemia cells, as compared to untreated mice and DBA/2 mice administered a formulation prepared with cancer cells and UV-inactivated MG1 virus.

In contrast, an immunogenic formulation according to the present disclosure, made using a live multi-attenuated glycoprotein mRNA deleted rhabdovirus (VSVd51ΔG), able to infect L1210 cells due to the retained presence of the glycoprotein on its capsular surface, resulted in viral GFP expression, as illustrated in FIG. 6b, which shows flow cytometry data of L1210 cells substantively infected after 18 and 72 hours incubation (MOI 10) with the GFP-tagged multi-attenuated G-glycoprotein mRNA+M51 deleted rhabdovirus. Viral spread is reduced using VSVd51ΔG since replication requires the mRNA encoded G-protein for final virion assembly and cell surface budding. When an immunogenic formulation according to the present disclosure was prepared using the live multi-attenuated virus, for example VSVd51ΔG, prolonged leukemic protection was observed in 80% of the recipient mice, as illustrated in FIGS. 6c and 15c, respectively. These results support the previous observation that immunogenic formulation-induced leukemic protection is not a consequence of enhanced immune recognition of γ-IR leukemic cells from simultaneous viral provocation. Rather, immune response appears to be required from a live translationally competent virus, even if the virus is incapable of fully completing its lifecycle. Moreover, in contrast to virus monotherapy for solid tumors where viral spread is tumoricidal, these results suggest that using a multi-attenuated replication incompetent virus might further increase the therapeutic index of the immunogenic formulation.

Pre-Existing Virus-Neutralizing Antibodies do not Alter the Immunogenic Formulation-Induced Immune Response.

Figure 6D:
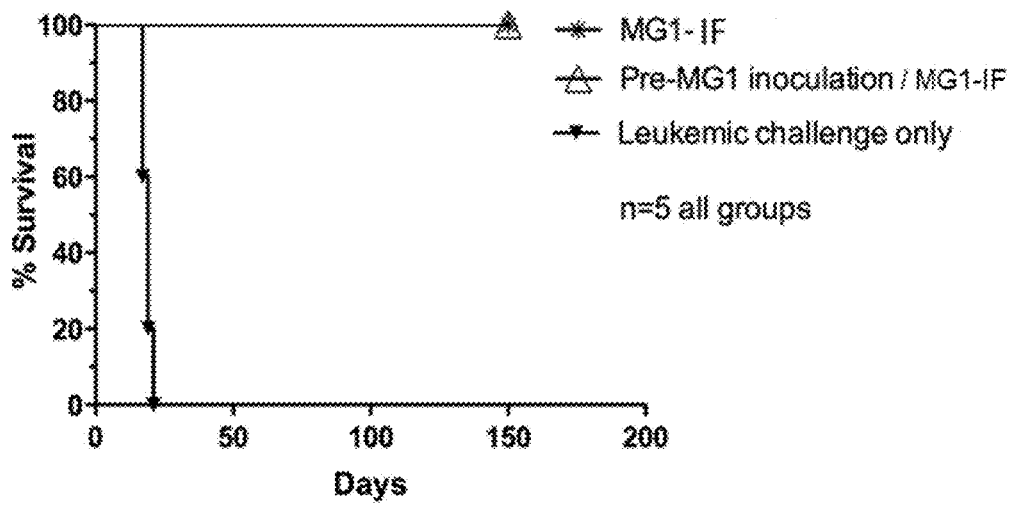

The development of anti-viral antibodies is often considered an impediment to oncolytic virus intra-tumoral spreading or delivery upon repeat dosing. To test the effect of pre-existing anti-viral antibodies, mice received MG1 ($10^7$ pfu by tail vein) with saphenous blood samples drawn before and 10 days after virus injection. Virus-neutralizing antibody titers were measured as negative and ≥1:800 respectively (5 bio-replicates). The initial dose of immunogenic formulation occurred 18 days after the MG1 injection. No survival differences were noted in this cohort compared to the group receiving immunogenic formulation without preceding MG1 inoculation, as illustrated in FIG. 6d, which shows the survival curve of MG1-naïve mice treated with an immunogenic formulation according to the present disclosure, compared to mice who received only the leukemic challenge, and mice receiving a pre-inoculation with MG1 as well as the immunogenic formulation. The above results suggest that circulating anti-viral antibodies do not significantly neutralize the immunogenicity of the immunogenic formulation.

Dosing Schedule.

Preliminary studies suggest that repeated dosing schedule improves the efficacy of the immunogenic formulation.

Leukemic Protection Induced by the Immunogenic Formulation May be Due to Adaptive T-Cell Mediated Immune Response.

Adoptive splenocyte transfer from long-term survivors previously treated with an exemplary immunogenic formulation protects naïve recipients from subsequent leukemic challenge. Long-term survival due to anti-tumor protection and surveillance may be due to the development of adaptive cell-mediated immune response. Without being bound by theory, it is believed that this may be due to a functional thymocyte compartment having both cytotoxic (CD8+) and helper (CD4+) T-cell populations.

Figure 7:
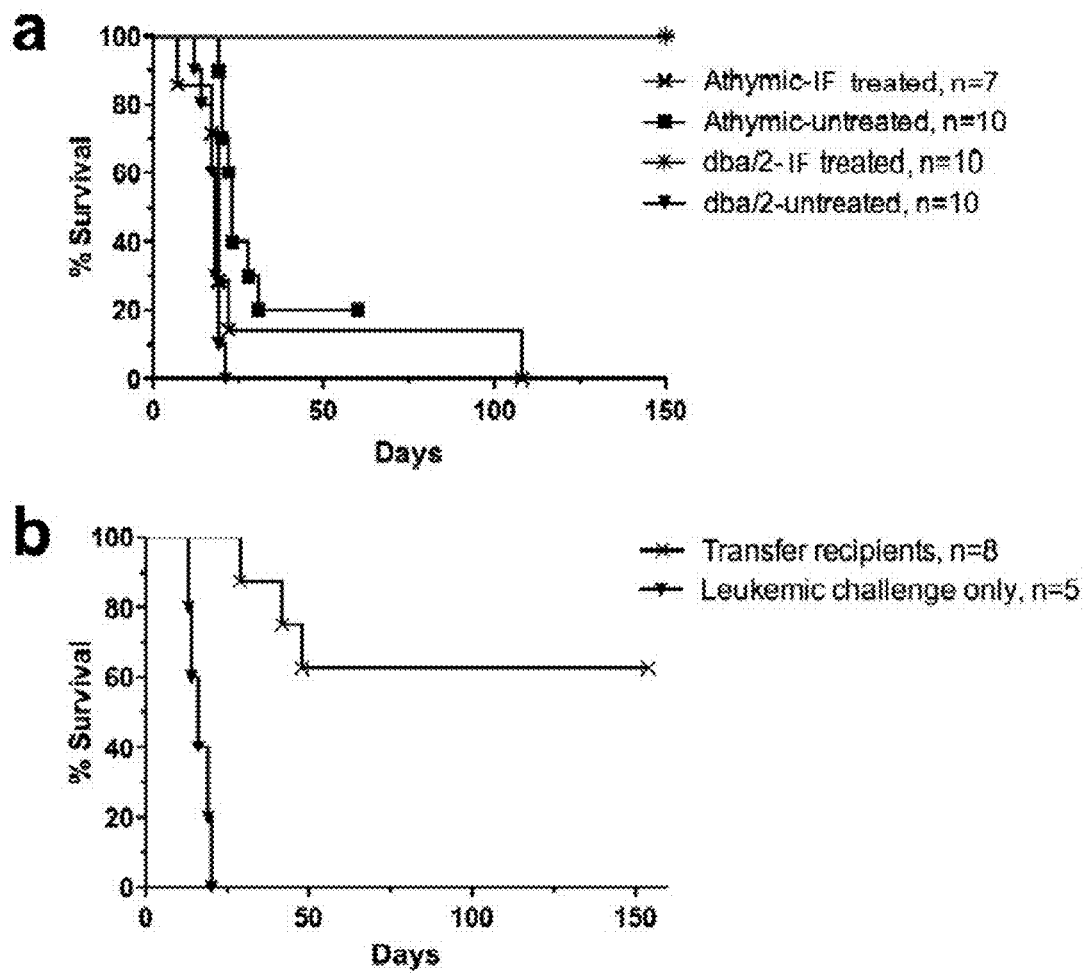
FIG. 7a is a graph showing survival curves of athymic nude mice which have been administered an immunogenic formulation according to the present disclosure prior to leukemic challenge, compared to immune competent mice that have been administered with an immunogenic formulation according to the present disclosure.
FIG. 7b shows the survival curve of 8 naïve dba/2 mice that received pooled adoptive splenocyte transfer from 17 donors that had previously received an immunogenic formulation according to the present disclosure.

Nude mice have a deletion in the FOXNI gene, which results in athymia with significantly reduced numbers of mature T-cells. To determine whether treatment with the immunogenic formulation invokes T-cells for efficacy, nude mice were compared to the model dba/2 mice. As opposed to the immune competent control mice, athymic mice were not sufficiently protected from leukemic challenge, as illustrated in FIG. 7a, which shows the survival curve of athymic nude mice which have been administered the exemplary immunogenic formulation prior to leukemic challenge, compared to immune competent mice that have been administered the exemplary immunogenic formulation.

The spleen is the principle repository of mature murine effector memory lymphocytes. In order to examine the effect of adoptive splenocyte transfer from long-term immunogenic formulation-protected mice to naïve recipients, 17 mice having survived between 211-349 days post leukemic challenge were used as pooled splenocyte donors for 8 naïve dba/2 recipients. Leukemic challenge occurred 7 days after splenocyte transfer. Survival was prolonged in the mice with long-term survival (154 days) in 63% of the recipients, as illustrated in FIG. 7b, which shows the survival curve of 8 naïve dba/2 mice that received pooled adoptive splenocyte transfer from 17 donors that had previously received an immunogenic formulation according to the present disclosure.

Figure 8:
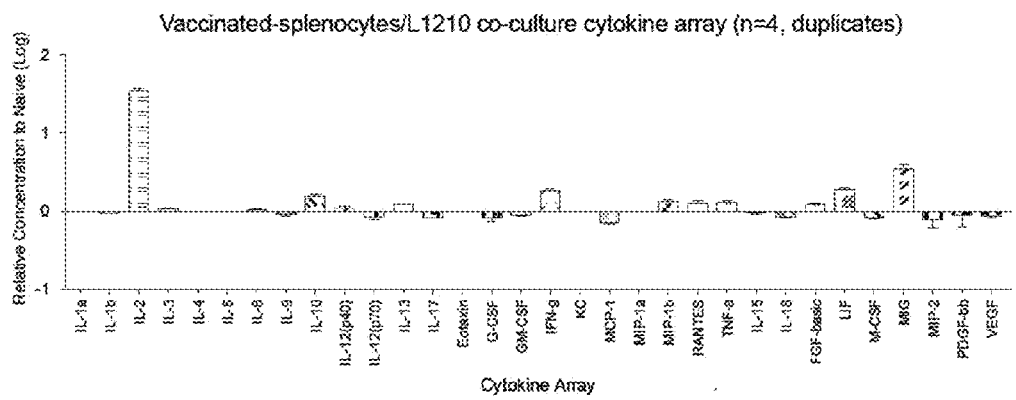
FIG. 8 is a graph showing a cytokine array or cytokine profile.

To further characterize the splenocyte immune response generated after treatment with the immunogenic formulation, a quantitative 32-cytokine array was performed. Splenocytes were co-cultured with target L1210 cells. Relative to untreated control mice; immunogenic formulation-educated splenocytes secreted over 1.5 logarithms higher IL-2, as illustrated in FIG. 8, which is a graph showing a cytokine array or cytokine profile of L1210 splenocytes in co-culture with L1210 cells (immunogenic formulation-educated splenocytes) cells infected with MG1 virus. The relative concentration to uninfected to naïve control murine L1210 cells is shown as a function of the different cytokines of the cytokine array. To a lesser extent, monokine induced by interferon gamma (MIG), leukemia inhibitory factor (LIF), IL-10 and interferon-gamma were also increased, as seen in FIG. 8.

Virus Treatment of Leukemia.

Figure 9:
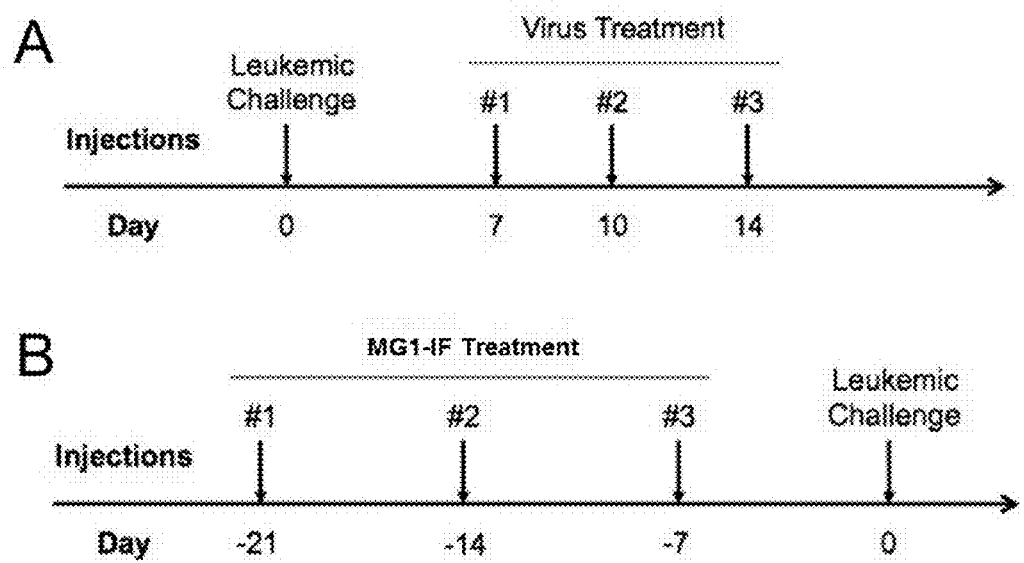
FIG. 9 A and B are graphs illustrating an exemplary treatment schedule for an immunogenic formulation according to the present disclosure.

DBA/2 mice received tail-vein injections of $1\times10^6$ L1210 leukemia cells. Leukemic mice were treated with 100 µL PBS or PBS containing $1\times10^8$ plaque forming units (pfu) MG1 by tail vein injection 7, 10 and 14 days later (FIG. 9A). The maximum tolerable dose (MTD) of MG1 administered by this schedule was previously determined to be about $1\times10^8$ pfu. Mice were euthanized upon development of typical signs of advanced leukemia such as hind-leg paralysis, focal tumor development, significant weight loss and/or respiratory distress.

Administration of an Immunogenic Formulation and Leukemic Challenge.

Administration was by tail vein injection of 100 µL per mouse per dose of a freshly prepared immunogenic formulation according to the present disclosure, an alternative formulation, or PBS. An exemplary treatment protocol is illustrated in FIG. 9B, which shows administration once weekly for a total of 3 doses, followed by a challenge one week later by intravenous tail vein injection of viable leukemia cells from suspension cultures. Cells were pelleted by centrifugation, media aspirated, washed once in PBS and resuspended at $1\times10^7$ cells/ml in PBS. Mice received a dose of $1\times10^6$ cells unless otherwise specified. Mice were euthanized upon the development of predetermined signs of advanced leukemia endpoints.

Adoptive Cell Transfer.

Single cell suspensions of splenocytes were prepared from spleens removed from donor mice using gentleMACS Dissociator (Miltenyi Biotec, Auburn, Calif.) according to manufacturer's recommendations under sterile conditions. The donor mice were naïve DBA/2 mice, or mice previously administered an immunogenic formulation according to the present disclosure. Cells from several donors were pooled and $15\times10^7$ donor splenocytes were injected intravenously via tail vein into syngeneic recipients. Splenocyte recipients received a leukemia challenge of $1\times10^6$ L1210 cells, administered intravenously via tail vein, one week after adoptive transfer.

Flow Cytometry.

Leukemia cell infections were evaluated by flow cytometric analysis of 10,000 cells using Quanta SC (Beckman Coulter). A 500 µL aliquot of infected cells was stained with 5 µL PI (1 mg/mL) approximately 30 minutes before data acquisition. The immunogenic formulations were analyzed by flow cytometry in similar fashion to allow dose standardization and quality control of virus expression. For analysis of apoptosis and necrosis, acquisition was performed on Cyan ADP (Beckman Coulter) using the Annexin V apoptosis detection kit APC and cell viability dye, 7-AAD, with minimum of 50,000 cells counted. Data analysis was performed with Kaluza software version 1.1 (Beckman Coulter) and Cell Lab Quanta Analysis (Beckman Coulter).

Statistics.

Survival curves were generated using product limit (Kaplan-Meier) method and comparisons were performed using log-rank (Mantel-Cox) test. All P values are two-tailed. Statistical significance was determined at level of P<0.05. Analyses were performed using Prism 5 software (GraphPad Software, La Jolla Calif.).

Results

MG1 Virus Infects Leukemia Lines In Vitro but is Ineffective in Halting Leukemia Progression In Vivo.

Figure 10A:
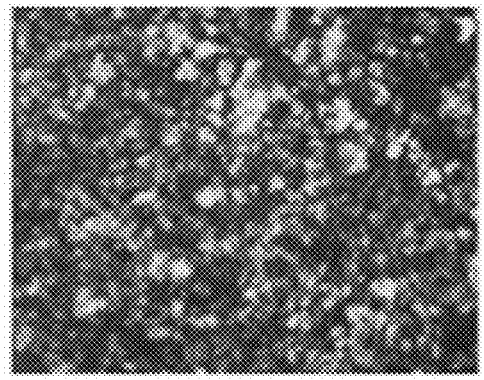
FIG. 10a is a fluorescence microscopy images showing cellular expression of viral GFP after infection with MG1-GFP in human T-cell leukemia cell lines.
Figure 10A:
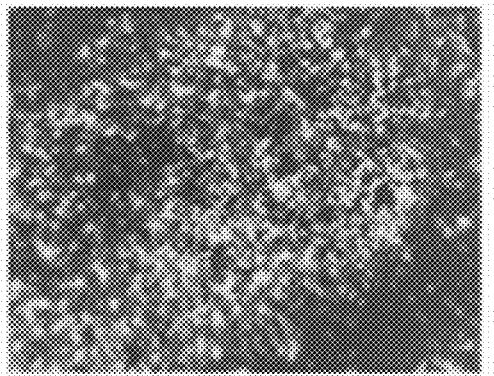
Figure 10A:
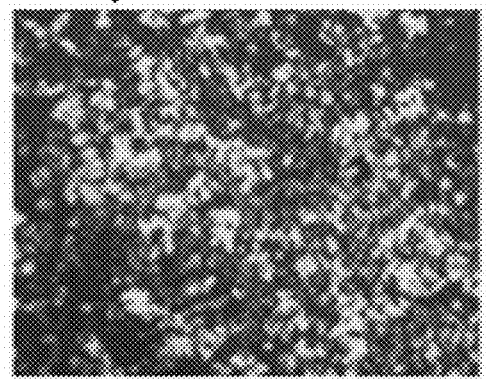
Figure 10A:
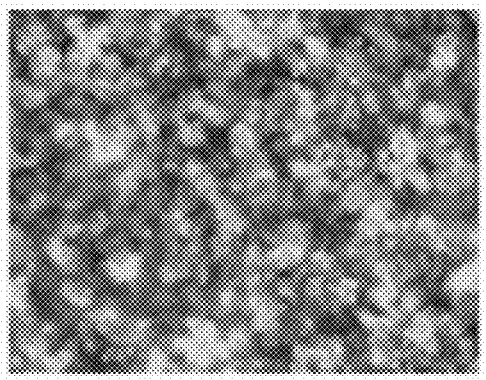
Figure 10A:
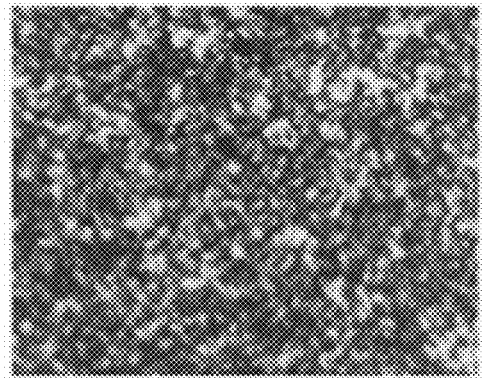
Figure 10B:
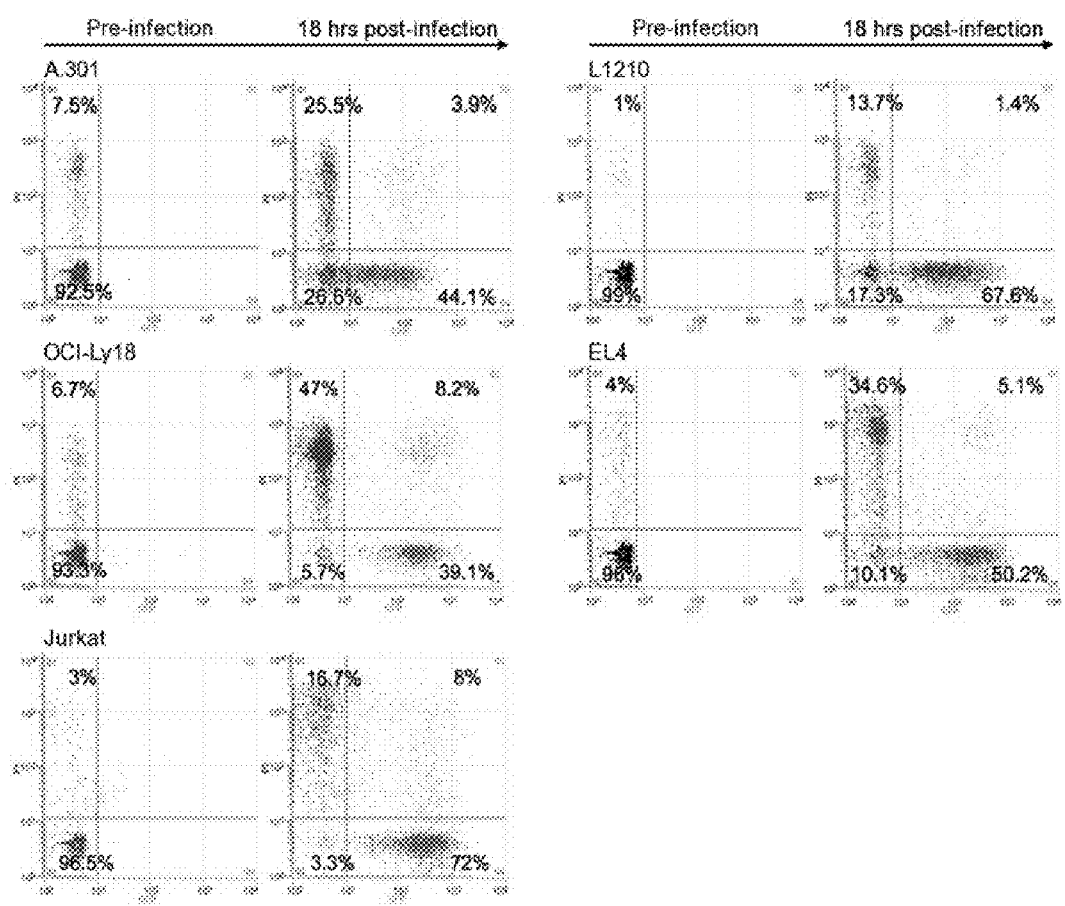
FIG. 10b are graphs of flow cytometry data of the cells lines shown in FIG. 10 A.
Figure 10C:
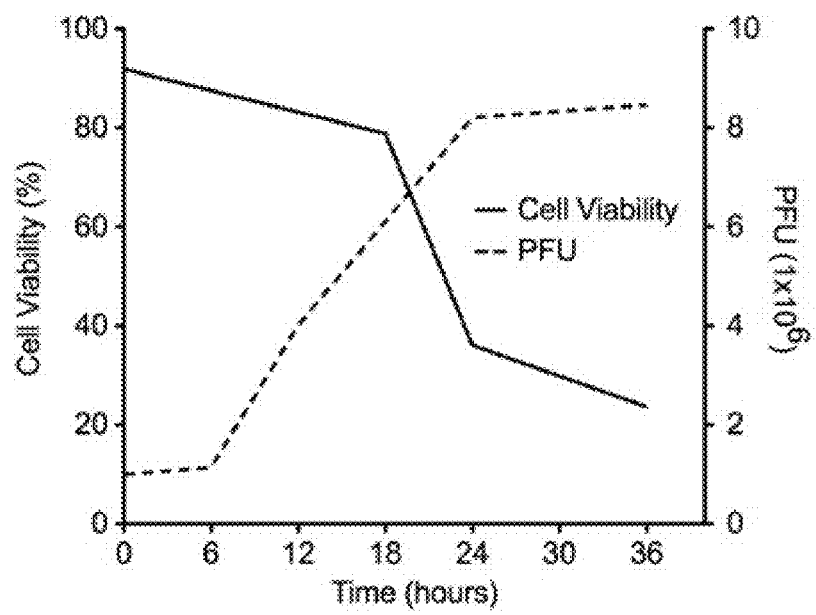
FIG. 10c is a graph illustrating cell viability of L1210 cells versus virus enumeration by viral plaque forming units (PFU) over time following infection with MG1 at low MOI (0.1).

We first wished to explore whether mice with disseminated acute lymphoblastic leukemia (ALL) could be successfully treated by systemic delivery of an oncotropic rhabdovirus. We first established that MG1 was able to infect and kill various murine and human leukemia cell lines in-vitro at low MOI (FIGS. 10a and 10b). L1210 leukemia cells demonstrate considerable permissiveness to MG1 infection and in vitro administration resulted in efficient, rapid cytolysis though virus production is modest over 24-40 hours incubation (FIG. 10c).

Figure 10D:
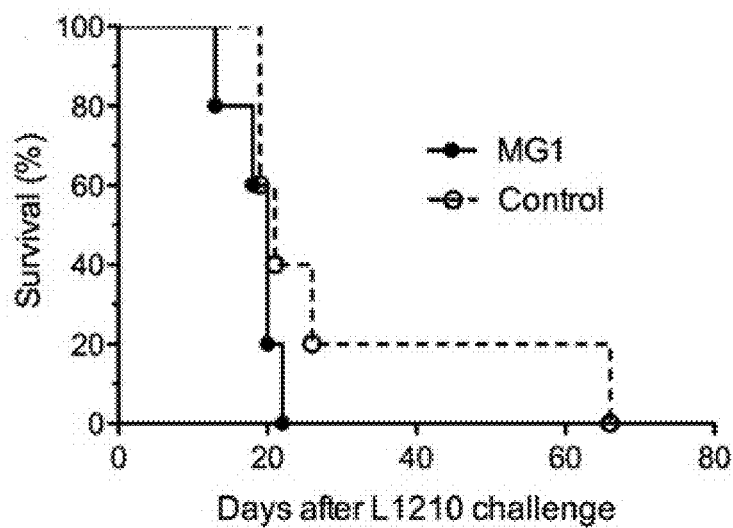
FIG. 10d is a graph illustrating a survival curve of DBA/2 mice which have established L1210 leukemia and are systemically treated with MG1 compared to untreated mice.

We previously determined the maximum tolerable dose (MTD) of a single intravenous administration of MG1 to be approximately $1\times10^9$ pfu. Therefore a cohort of mice was given $1\times10^8$ pfu of MG1-eGFP daily every 3 days for 3 doses. One of 5 mice died 3 days following the second virus injection. The presence of virus (eGFP) was detected in liver and brain homogenates, indicating the multi-dose MTD for future experiments. Accordingly, seven days after establishing L1210 leukemia, mice received 3 doses of $1\times10^8$ pfu MG1 via tail vein injection. Administration of virus in vivo was unable to prevent disease progression (FIG. 10d) and the mice succumbed with evidence of overwhelming leukemia. Autopsy studies were performed and infectious MG1 was not recovered from liver or brain homogenates of L1210 challenged mice treated with virus. These results suggest that despite the ability of MG1 to infect and kill leukemia cells in vitro, barriers exist preventing effective systemic cytolytic virotherapy of high burden ALL.

Immunogenic Formulations According to the Present Disclosure and Leukemia Challenge.

Figure 11A:
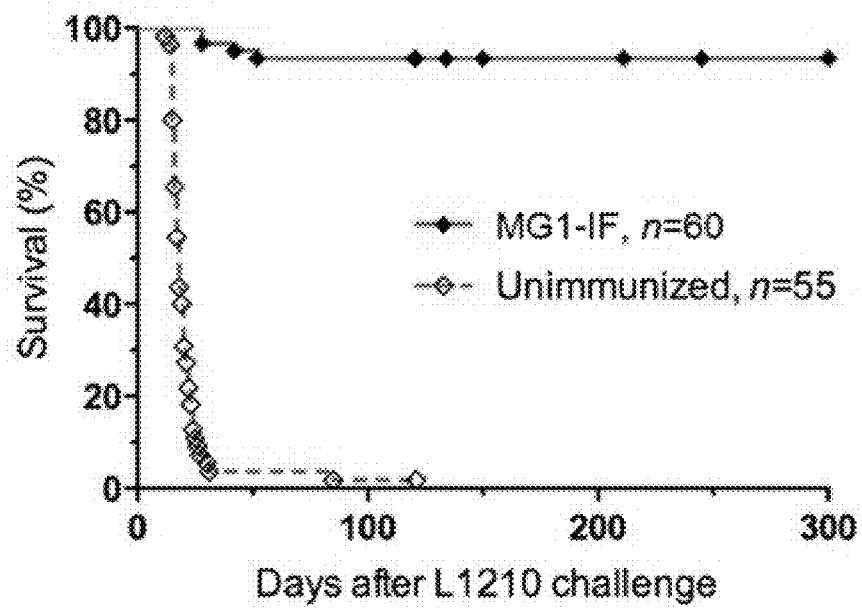
FIG. 11a is a graph illustrating survival curves of DBA/2 mice administered an immunogenic formulation according to the present disclosure and challenged with L1210 leukemic cells, as compared to unimmunized mice.
Figure 11B:
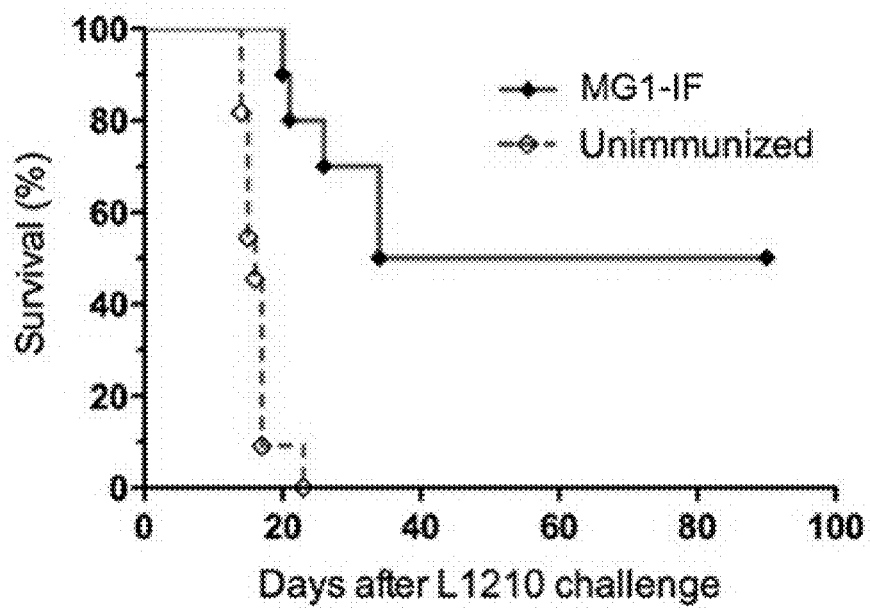
FIG. 11b is a graph illustrating survival curve of administered an immunogenic formulation according to the present disclosure and challenged with a high dose of L1210 leukemic cells, as compared to unimmunized mice.

Mice were administered 3 weekly doses of γ-IR virus-infected L1210 cells (MG1-IF), one example of an immunogenic formulation according to the present disclosure. This was followed, a week later, by injection of viable L1210 cells. Mice that received MG1-IF demonstrated greater than 90% long term survival following challenge with viable leukemia cells compared to untreated control mice which reproducibly reached leukemic end-points with median survival of 18 days (FIG. 11a). When leukemic challenge was administered one day prior to series of administration of the MG1-IF, 100% of control mice succumbed to leukemia, whereas 50% of mice that received MG1-IF survived (FIG. 11b). Without being bound by theory, it is believed that this incomplete protection is due to rapid growth of L1210 leukemia in this aggressive tumor model, which outstrips the development of the anti-tumor response.

Figure 12A:
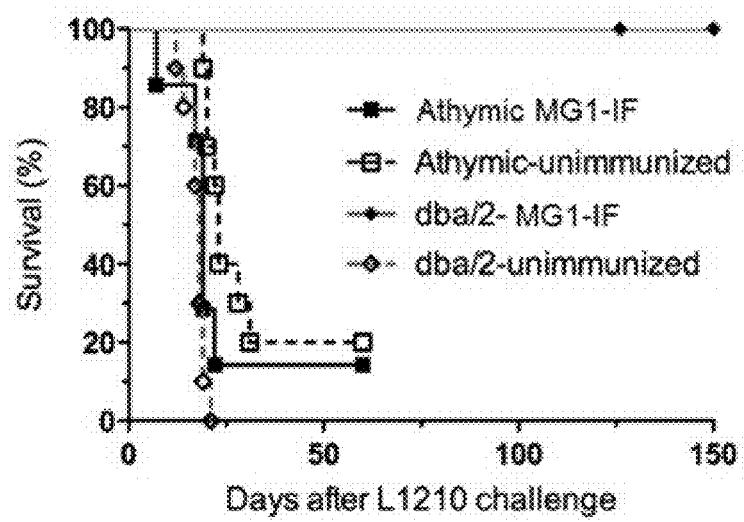
FIG. 12a is a graph illustrating a survival curve of immunocompetent DBA/2 mice administered an immunogenic formulation according to the present disclosure and challenged with L1210 leukemia cells, as compared to immunodeficient athymic mice.

To test whether the protective effects of the MG1-IF were mediated through development of anti-tumor immune response, MG1-IF was administered to athymic nude or immunocompetent DBA/2 mice once weekly for 3 doses. Treated and untreated nude mice died from leukemia a median of 18 and 23 days respectively following injection of viable L1210 cells. In contrast, immunocompetent mice that received MG1-IF rejected L1210 cells (FIG. 12a).

Figure 12B:
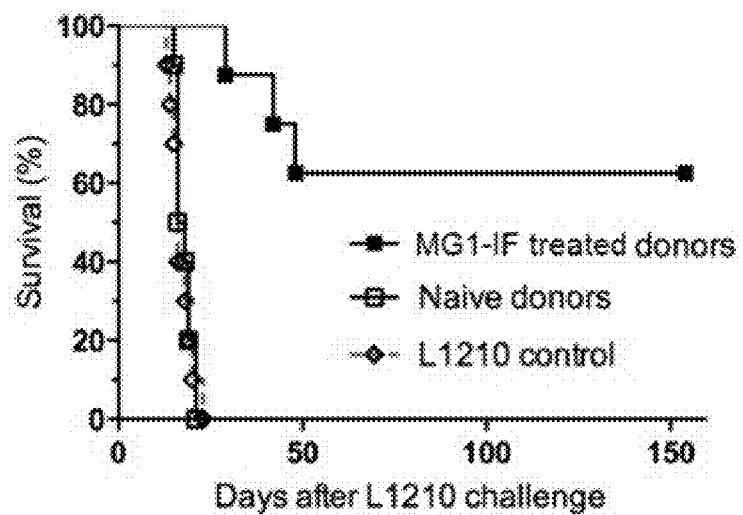
FIG. 12b is a graph illustrating a survival curve of naïve DBA/2 recipient mice of splenocytes from DBA/2 mice donors which had been administered an immunogenic formulation according to the present disclosure, as compared to naïve DBA/2 recipient mice of splenocytes from untreated DBA/2 mice donors.

In a separate experiment, we wished to examine the effect of adoptive splenocyte transfer from mice donors which had previously been administered an immunogenic formulation according to the present disclosure to naïve recipients. Accordingly, 17 mice that had received MG1-IF and survived between 211-349 days following a leukemic challenge were used as splenocyte donors. The pooled donor splenocytes were administered to 8 naïve DBA/2 recipients followed 7 days later by injection of viable L1210 cells. Long-term survival was observed in 63% of these recipients, while control mice that received the same number of splenocytes from untreated donors were unable to reject leukemic challenge (FIG. 12b). Collectively, these experiments indicate that the protection afforded by immunogenic formulations according to the present disclosure is mediated by an intact immune system.

Figure 12C:
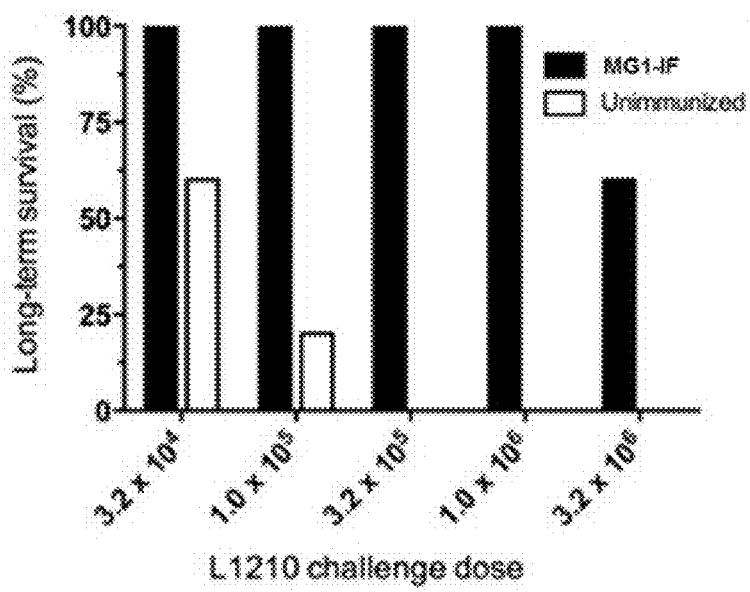
FIG. 12c is a graph illustrating survival of DBA/2 mice administered an immunogenic formulation according to the present disclosure and challenged with increasing doses of L1210 leukemia cells, as compared to untreated mice.
Figure 12D:
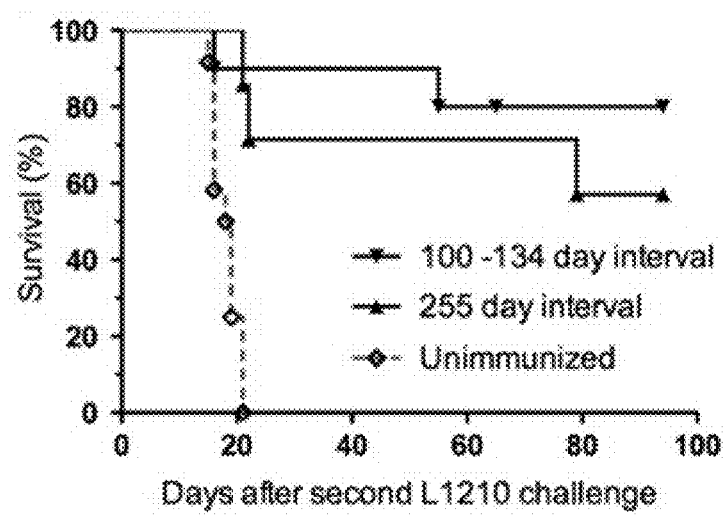
FIG. 12d is a graph illustrating a survival curve of mice administered an immunogenic formulation according to the present disclosure and subjected to a second challenge with L12010 leukemia cells either 100-134 days or 255 days after a first challenge with L1210 leukemia cells.

To examine the strength of the immune response that develops following administration of an immunogenic formulation according to the present disclosure, cohorts of unimmunized and MG1-IF treated mice were challenged with increasing amounts of viable L1210 cells. The $LD_{50}$ of unimmunized mice was approximately $4.9\times10^4$ cells while the $LD_{50}$ for MG1-IF vaccinated mice was estimated to be $3.8\times10^6$ cells. Thus, administration of MG1-IF was able to protect mice against an almost 100 fold larger inoculum of leukemia than would be spontaneously rejected by unimmunized mice (FIG. 12c). The durability of such a response may have particular benefit as the ability to prevent leukemic recurrence may wane over time. Mice administered MG1-IF that survived a primary leukemic challenge were administered a second L1210 leukemia challenge either 100, 134, or 255 days after initial L1210 challenge. The majority of mice were able to reject this additional leukemic challenge, but there may be a time-dependent decline in the ability to reject a late secondary leukemic challenge (FIG. 12d).

Figure 13:
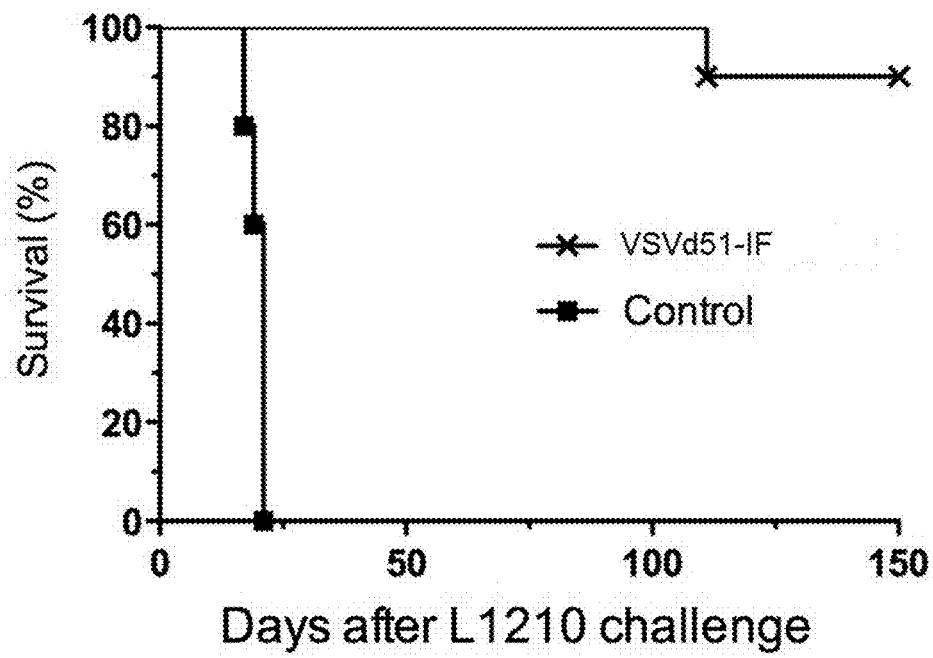
FIG. 13 is a graph illustrating the survival curve of DBA/2 mice administered an immunogenic formulation according to the present disclosure and challenged with an injection of $1 \times 10^6$ L1210 leukemia cells, as compared to untreated mice.
Figure 14:
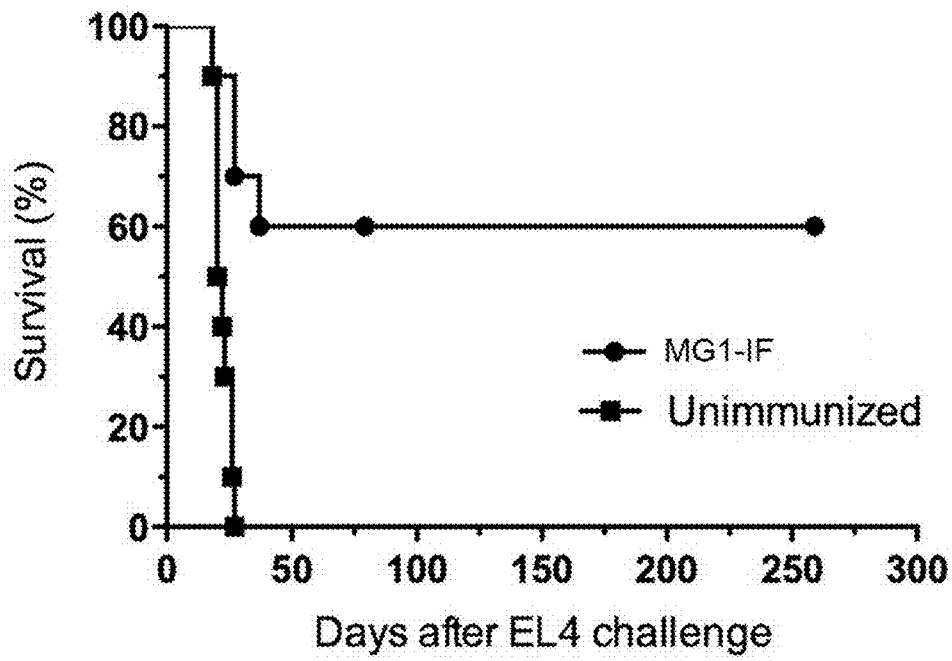
FIG. 14 is a graph illustrating the survival curve of C57BL/6 mice administered an immunogenic formulation according to the present disclosure and challenged with an injection of $1 \times 10^6$ EL4 leukemia cells, as compare to untreated mice.

Immunogenic formulations according to the present disclosure are not limited to a single rhabdovirus, leukemic cell line or mouse strain. Survival following leukemic challenge was observed when animals were administered an immunogenic formulation prepared using a different rhabdovirus—VSVd51, indicating that the protective effects were independent of the specific rhabdovirus (FIG. 13). Similarly, mice survived an otherwise lethal challenge with EL4, a T lymphoma cell line, when MG1-IF prepared using these cells were administered to syngeneic C57Bl/6 mice (FIG. 14).

Figure 12E:
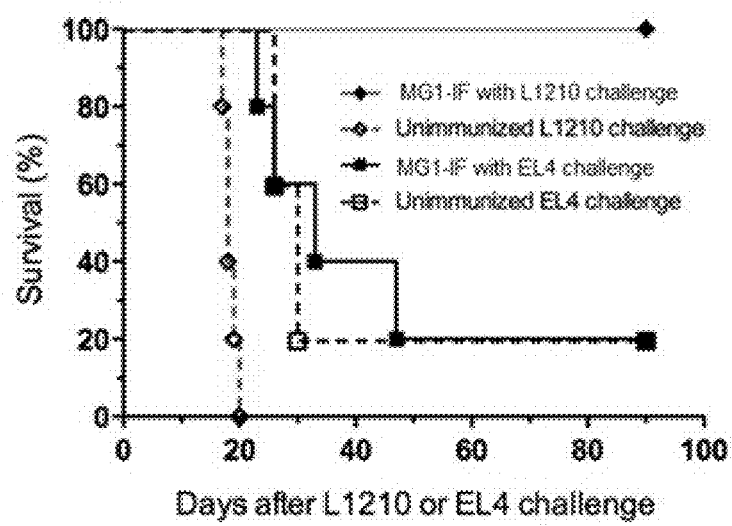
FIG. 12e is a graph illustrating the survival curve of mice administered an immunogenic formulation according to the present disclosure and challenged with either L1210 or EL4 leukemic cells, as compared to untreated mice challenged with either L1210 or EL4 leukemic cells.

To examine the specificity of the anti-tumor protection afforded by MG1-IF, two cohorts of B6D2F1 hybrid mice were administered 3 weekly doses of MG1-L1210 IF. One cohort was subsequently challenged with viable $1\times10^7$ L1210 cells while the other received $1\times10^7$ EL4 cells. Mice that received the L1210-based immunogenic formulation were protected from L1210 challenge, while survival of EL4 challenged mice was identical to unimmunized mice challenged with EL4 (FIG. 12e). This observation suggests that immunogenic formulations according to the present disclosure induce anti-tumor immune response to the specific antigenic profile of the leukemic cell used to produce the immunogenic formulation, rather than commonly expressed leukemic antigens.

Virus Infection and Induction of IF-Mediated Anti-Leukemic Immune Response.

We examined whether the cellular and viral components of an immunogenic formulation according to the present disclosure could be individually effective at inducing protective anti-tumor immune response. Mice administered 3 doses of γ-IR ex vivo MG1 infected L1210 cells (MG1-IF) survived subsequent administration of an otherwise lethal dose of L1210 cells, while the mice that received γ-IR uninfected L1210 cells prior to leukemic challenge succumbed with median survival that was not significantly different from unimmunized mice that received the same leukemic challenge dose. Furthermore, 3 weekly separate co-injections of γ-IR L1210 cells and MG1, or the administration of 3 weekly doses of γ-IR L1210 cells mixed with MG1 at room temperature for 1 hour prior to injection, were unable to prevent the lethality of a subsequent L1210 leukemia challenge (FIG. 15a).

Figure 15D:
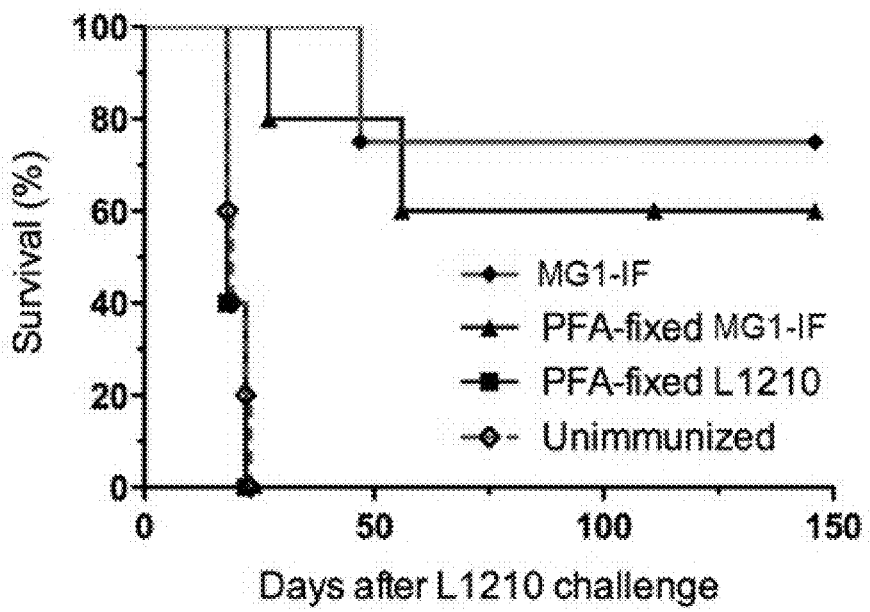
FIG. 15d is a graph illustrating a survival curves of DBA/2 mice administered immunogenic formulations according to the present disclosure and challenged with L1210 leukemia cells, as compared to untreated mice or mice treated with control formulation.

In vitro, leukemic cells exposed to UV-inactivated MG1-eGFP virus did not express GFP, nor did they develop cytopathology. In contrast, L1210 cells exhibit green fluorescence following in vitro exposure to live-attenuated spread-incompetent VSVd51ΔG-eGFP, and delayed cytolysis occurs as long as 72 hours after infection (FIG. 15b). Immunization with an immunogenic formulation produced by infection of L1210 cells with VSVd51ΔG protected 80% of mice from the lethal effects of subsequent L1210 challenge (FIG. 15c), indicating that the immunogenic formulation is effective even if the virus is incapable of fully completing its lifecycle. Administration of a formulation produced with UV-inactivated MG1 prior to challenge with viable L1210 leukemia was unable to prevent death from fulminant leukemia in 80% of mice. Formulations fixed with PFA after virus infection but immediately prior to γ-IR were capable of protecting immunized mice just as effectively as freshly produced, unfixed formulations (FIG. 15d). PFA-fixed formulations did not contain detectable viable MG1 in a standard plaque assay. Thus, in this model, viable rhabdovirus appears to be necessary for the manufacturing of immunogenic formulations but viability of the virus is not critical at the time of therapeutic administration.

MG1-IF Compared to Activation of Anti-Viral Defense Pathways.

Figure 16A:
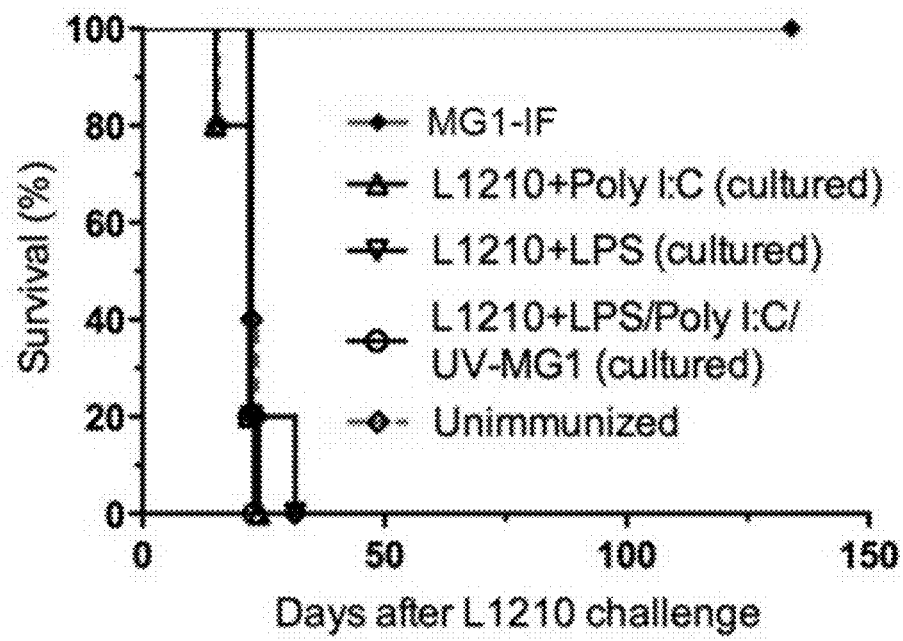
FIG. 16a is a graph illustrating survival curves of DBA/2 mice administered an immunogenic formulation according to the present disclosure and challenged with L1210 leukemia cells, as compared to untreated mice, mice administered a formulation of L1210 cells cultured in LPS or poly I:C, or mice administered a formulation of L1210 cells cultured in LPS and poly I:C and UV-inactivated MG1 virus.

The immune stimulatory effects induced by administration of ex-vivo virus infected leukemia cells cannot be mimicked solely by activation of anti-viral defense pathways in leukemia cells used for immunization. L1210 cells were cultured for 18 hours with poly I:C, LPS or both prior to γ-IR and injection. Mice that received 3 weekly injections of these preparations succumbed to subsequent injection of L1210 cells, in contrast to mice that received MG1-IF (FIG. 16a).

Figure 16B:
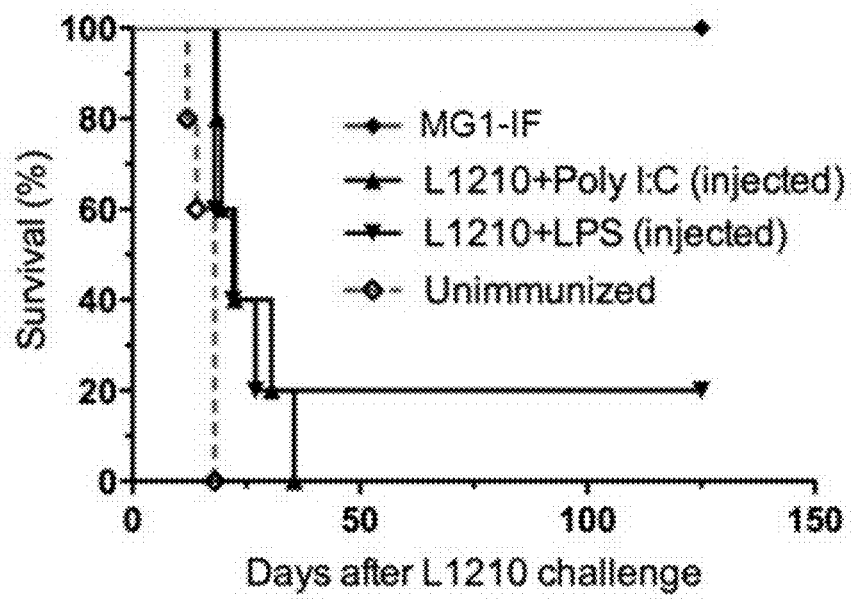
FIG. 16b is a graph illustrating survival curves of DBA/2 mice administered an immunogenic formulation according to the present disclosure and challenged with L1210 leukemia cells, as compared to untreated mice, or mice administered L1210 cells co-injected with LPS or poly I:C.

Pulsed stimulation of host innate immunity by direct injection of either poly I:C or LPS concurrently with 3 weekly injections of γ-IR L1210 cells was also incapable of protecting animals from subsequent injection of viable L1210 cells (FIG. 16b).

Figure 16C:
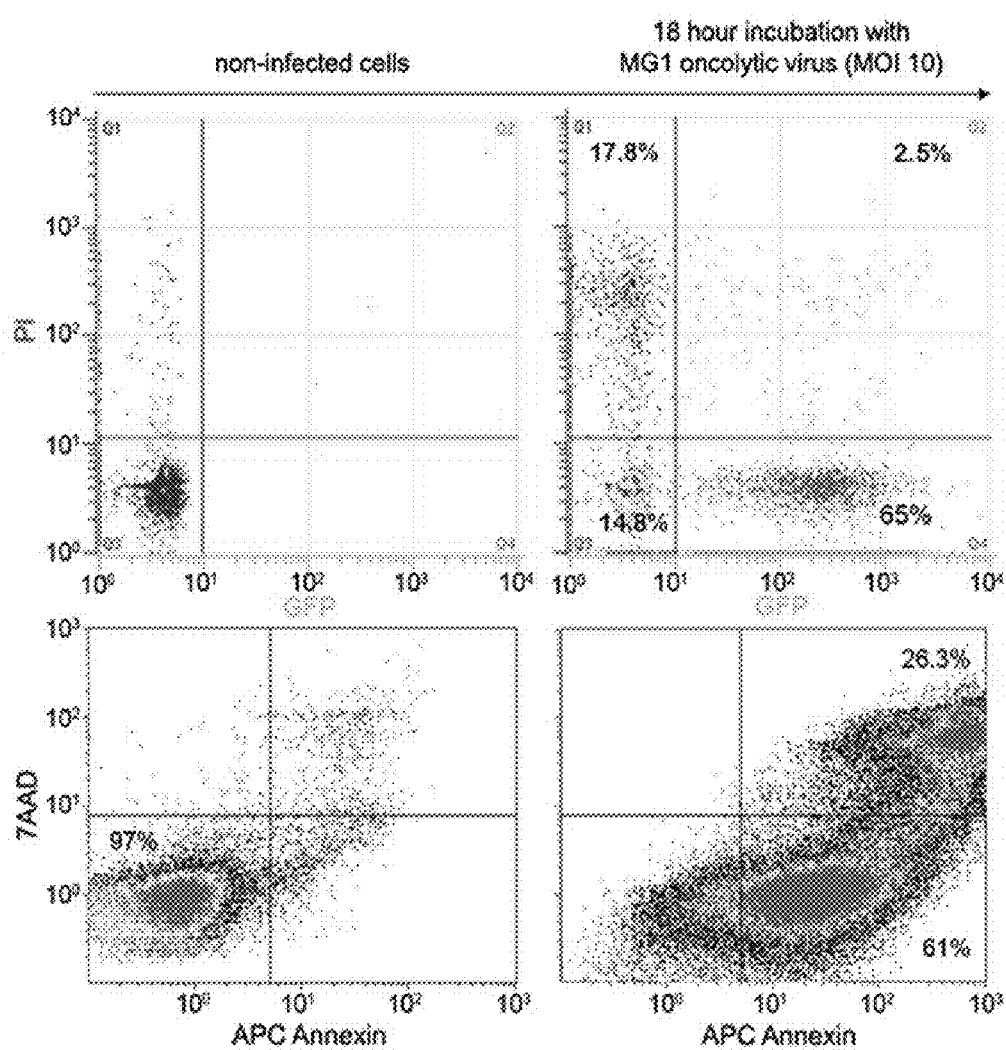
FIG. 16c shows graphs of flow cytometry data using cell viability dye 7-AAD to show apoptosis and necrosis of non-infected cells as compared to cells infected with MG1 virus.
Figure 16D:
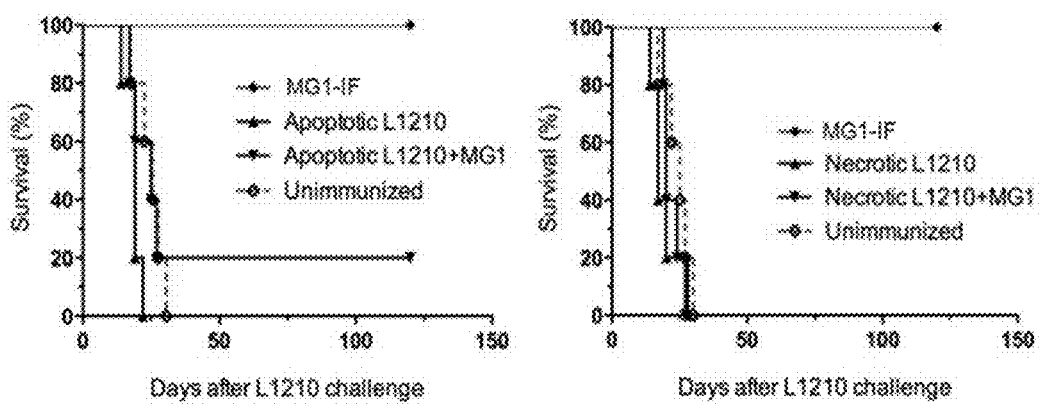
FIG. 16d shows graphs illustrating survival curves of DBA/2 mice administered an immunogenic formulation according to the present disclosure and challenged with L1210 leukemia cells, as compared to mice administered apoptotic or necrotic L1210 cells with or without additional MG1 virus.
Figure 17:
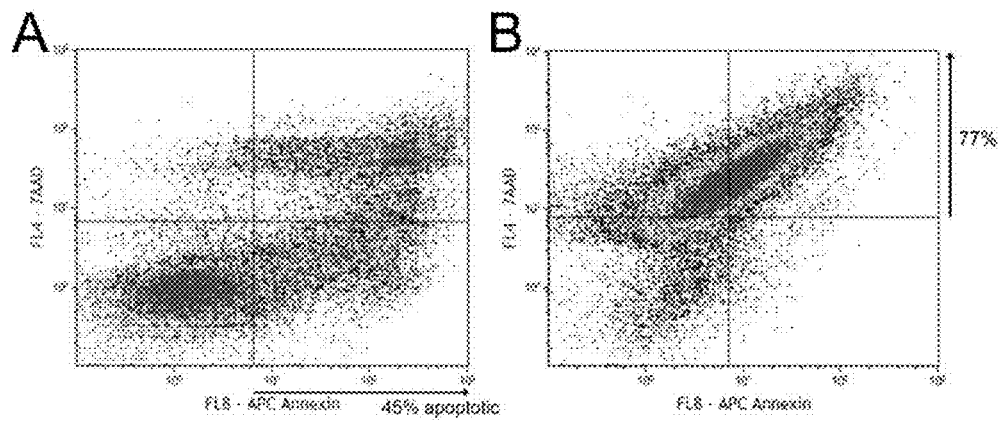
FIG. 17 shows flow cytometry data of L1210 cells stained with Annexin V-APC versus 7-AAD cell viability dye. In panel A, UVC-induced early apoptosis (Annexin V-APC+) and late apoptosis (Annexin V-APC+ and 7-AAD+) observed in L1210 cells 4 hours after the UVC treatment of cells is shown. In panel B, pressure disruption of L1210 cells (1500 PSI) is shown.

Similarly, the protective effects induced by injection of ex-vivo virus infected leukemia cells cannot be mimicked solely by the presence of apoptotic or necrotic cells. Apoptosis was induced in L1210 cells by UV irradiation (FIG. 17, panel A) while parallel samples of L1210 were pressure disrupted into cellular necrosis (FIG. 17, panel B). Cohorts of mice received 3 weekly injections of either MG1-IF, UV-irradiated apoptotic L1210, or pressure-disrupted necrotic L1210 followed by challenge of viable L1210 leukemia. Mice that received UV-irradiated or pressure disrupted L1210 expired due to leukemia in contrast to the mice that received MG1-IF. Administration of 3 weekly injections of apoptotic or necrotic L1210 cells mixed with MG1 virus just prior to injection, were similarly ineffective (FIGS. 16c and d).

Pre-Existing Anti-Viral Immune Response does not Impair Development of Anti-Leukemia Immune Response.

Figure 18:
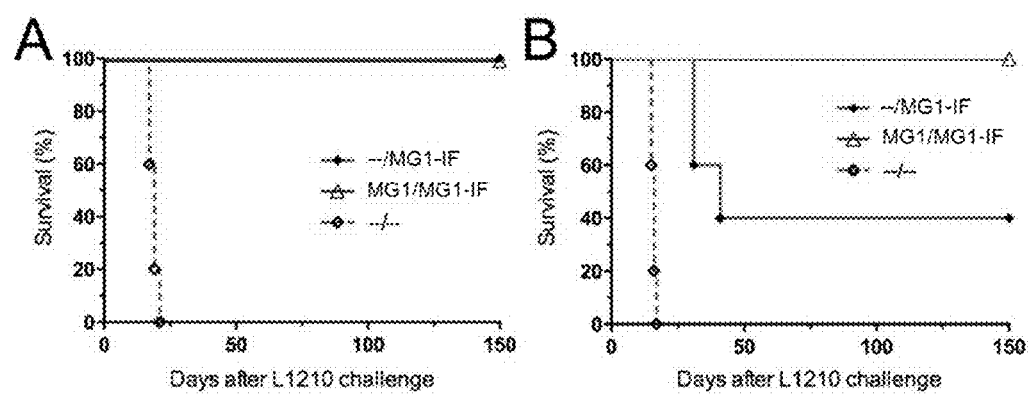
FIG. 18 shows graphs illustrating survival curves. Panel A illustrates the survival curve of DBA/2 mice previously administered MG1 virus and then administered an immunogenic formulation according to the present disclosure and challenged with $1 \times 10^6$ L1210 leukemia cells, as compared to untreated mice or mice not previously administered MG1 virus but administered an immunogenic formulation according to the present disclosure. Panel B illustrates the survival curve of DBA/2 mice previously administered MG1 virus and then administered an immunogenic formulation according to the present disclosure and challenged with $1 \times 10^7$ L1210 leukemia cells, as compared to untreated mice or mice not previously administered MG1 virus but administered an immunogenic formulation according to the present disclosure.

Mice were injected $10^7$ pfu MG1 by tail vein to generate an anti-viral immune response. Prior to receiving MG1, mice did not manifest serum virus-neutralizing antibody while the titer of MG1 neutralizing antibody was 1:800 in serum of mice 10 days following administration of virus. Three doses of MG1-IF were administered starting 18 days after MG1 injection. The survival of MG1 immunized mice was no different than a cohort of mice that received MG1-IF without preceding MG1 inoculation when challenged with $1\times10^6$ L1210 cells (FIG. 18, panel A). However, when L1210 challenge was increased 10 fold, mice immunized against MG1 prior to MG1-IF treatment (MG1/MG1-IF) had a significant survival advantage over mice that received MG1-IF treatment alone (—/MG1-IF) (FIG. 18, panel B). These results suggest immune response to the immunogenic formulation is not dampened, and may be augmented, following development of an anti-viral immune response.

In the preceding description, for purposes of explanation, numerous details are set forth in order to provide a thorough understanding of the examples. However, it will be apparent to one skilled in the art that these specific details are not required.

The above-described examples are intended to be illustrative only. Alterations, modifications and variations can be effected to the particular examples by those of skill in the art without departing from the scope, which is defined solely by the claims appended hereto.

What is claimed is:

1. A method of preparing an immunogenic formulation for treating a patient, the method comprising:
   obtaining uninfected hematopoietic cancer cells from the patient;
   testing and quantifying the uninfected hematopoietic cancer cells from the patient for expression of CD40 on cells;
   infecting, ex-vivo, the obtained uninfected hematopoietic cancer cells with an oncolytic rhabdovirus that modulates the expression of endogenous immune regulatory molecules including CD40 to increase the immunogenicity of the infected hematopoietic cancer cells;
   incubating the infected hematopoietic cancer cells to generate infected hematopoietic cancer cells having increased immunogenicity;
   testing and quantifying the infected hematopoietic cancer cells in the formulation for expression of CD40 on cells; and
   formulating the rhabdovirus-infected hematopoietic cancer cells having increased immunogenicity into a formulation wherein, the concentration of infected hematopoietic cancer cells expressing CD40 is greater than the concentration of uninfected hematopoietic cancer cells expressing CD40.

2. The method according to claim 1, wherein the obtained uninfected hematopoietic cancer cells are infected with viral particles in a ratio of at least 1 viral particle to 100 hematopoietic cancer cells.

3. The method according to claim 1, wherein the obtained uninfected hematopoietic cancer cells are infected with viral particles in a ratio of at least 10 viral particles to 1 hematopoietic cancer cell.

4. The method according to claim 1, wherein the infected hematopoietic cancer cells are incubated for at least a single gene replication cycle of the virus.

5. The method according to claim 1, wherein the virus is a vesicular stomatitis virus, a maraba virus, a carajas virus, or a chandipura virus.

6. The method according to claim 5, wherein the virus has interferon dependent and independent attenuating deletions in the matrix and glycoprotein proteins, respectively.

7. The method according to claim 5, wherein the vesicular stomatitis virus is a Vesicular Stomatitis Indiana Virus which is modified to be sensitive to the antiviral effects of type I interferons.

8. The method according to claim 5, wherein the virus is vesicular stomatitis virus which is modified to reduce the ability of the virus to spread to other cells.

9. The method according to claim 8, wherein the virus is modified by deletion of the gene encoding G-protein.

10. The method according to claim 1, wherein the immune regulatory molecules are: cytokines released by the cell, immunomodulatory markers expressed on the cell surface, immunomodulatory molecules released by the cell, or any combination thereof.

11. The method according to claim 10, wherein the cytokines are: CCL5, CCL4, IL-6, interferon-γ, IL-2, IL-12, IL-15, or any combination thereof.

12. The method according to claim 10, wherein the immunomodulatory markers expressed on the cell surface further include: OX40 ligand, Inducible costimulator-ligand (ICOS-L), OX40 (CD134), ICOS (CD278), CD137, CD137 ligand, CD40 ligand, CD28, CD95, FAS, FAS ligand, calreticulin, or any combination thereof.

13. The method according to claim 1, wherein formulating the immunogenic hematopoietic cancer cells for administration to the patient comprises exposing the hematopoietic cancer cells to gamma irradiation.

14. The method according to claim 1, wherein formulating the immunogenic hematopoietic cancer cells for administration to the patient comprises treating the hematopoietic cancer cells with paraformaldehyde.

15. The method according to claim 1, wherein formulating the immunogenic hematopoietic cancer cells for administration to the patient comprises treating the hematopoietic cancer cells with paraformaldehyde and exposing the treated hematopoietic cancer cells to gamma irradiation.

16. The method according to claim 1, wherein said step of formulating occurs when the concentration of infected hematopoietic cancer cells expressing CD40 is greater than 23%.

17. The method according to claim 1, wherein said step of formulating occurs when the concentration of infected hematopoietic cancer cells expressing CD40 is about 10 times greater than the concentration of uninfected hematopoietic cancer cells expressing CD40.

* * * * *